United States Patent
Peterson et al.

(10) Patent No.: US 9,120,743 B2
(45) Date of Patent: Sep. 1, 2015

(54) INTEGRATED PROCESS FOR THE PRODUCTION OF ACRYLIC ACIDS AND ACRYLATES

(71) Applicant: Celanese International Corporation, Irving, TX (US)

(72) Inventors: Craig J. Peterson, Houston, TX (US); Elizabeth Bowden, Houston, TX (US); Josefina T. Chapman, Houston, TX (US); Sean Mueller, Pasadena, TX (US); Dick Nagaki, The Woodlands, TX (US); Tianshu Pan, Houston, TX (US); Himanshu Lodha, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/928,858

(22) Filed: Jun. 27, 2013

(65) Prior Publication Data

US 2015/0005529 A1    Jan. 1, 2015

(51) Int. Cl.
| | | |
|---|---|---|
| *C07C 67/347* | (2006.01) | |
| *C07C 45/38* | (2006.01) | |
| *C07C 51/353* | (2006.01) | |
| *C07C 51/46* | (2006.01) | |
| *C07C 51/48* | (2006.01) | |

(52) U.S. Cl.
CPC ............. *C07C 67/347* (2013.01); *C07C 45/38* (2013.01); *C07C 51/353* (2013.01); *C07C 51/46* (2013.01); *C07C 51/48* (2013.01)

(58) Field of Classification Search
CPC ..... A61K 38/07; A61K 31/4178; C07K 5/10; C07C 67/62; C07C 69/003; C07C 69/40; C07C 67/347; C07C 45/38; C07C 51/353; C07C 51/445
USPC .................. 514/18.8; 530/330; 548/312.7
See application file for complete search history.

(56) References Cited

U.S. PATENT DOCUMENTS

| | | | |
|---|---|---|---|
| 3,538,122 A | 11/1970 | Friedrichsen et al. | |
| 3,541,143 A | 11/1970 | Nakano et al. | |
| 3,865,873 A | 2/1975 | Oda et al. | |
| 4,165,438 A | 8/1979 | Schneider | |
| 4,276,197 A | 6/1981 | Vartuli et al. | |
| 4,866,194 A | 9/1989 | Glaeser et al. | |
| 4,892,856 A | 1/1990 | Kawajiri et al. | |
| 4,994,608 A | 2/1991 | Torrence et al. | |
| 5,001,259 A | 3/1991 | Smith et al. | |
| 5,026,908 A | 6/1991 | Smith et al. | |
| 5,144,068 A | 9/1992 | Smith et al. | |
| 5,364,824 A | 11/1994 | Andrews et al. | |
| 5,504,247 A | 4/1996 | Saxer et al. | |
| 5,523,480 A | 6/1996 | Bauer, Jr. et al. | |
| RE35,377 E | 11/1996 | Steinberg et al. | |
| 5,599,976 A | 2/1997 | Scates et al. | |
| 5,755,975 A | 5/1998 | Eck et al. | |
| 5,821,111 A | 10/1998 | Grady et al. | |
| 6,143,930 A | 11/2000 | Singh et al. | |
| 6,232,352 B1 | 5/2001 | Vidalin et al. | |
| 6,509,180 B1 | 1/2003 | Verser et al. | |
| 6,544,924 B1 | 4/2003 | Jackson et al. | |
| 6,627,770 B1 | 9/2003 | Cheung et al. | |
| 6,657,078 B2 | 12/2003 | Scates et al. | |
| 6,685,754 B2 | 2/2004 | Kindig et al. | |
| 6,852,881 B2 | 2/2005 | De Decker et al. | |
| 7,005,541 B2 | 2/2006 | Cheung et al. | |
| 7,053,147 B2 | 5/2006 | Jackson et al. | |
| 7,115,772 B2 | 10/2006 | Picard et al. | |
| 7,208,624 B2 | 4/2007 | Scates et al. | |
| 7,300,555 B2 | 11/2007 | Schroeder et al. | |
| 7,307,189 B2 | 12/2007 | Eck et al. | |
| 7,351,559 B2 | 4/2008 | Verser et al. | |
| 7,507,562 B2 | 3/2009 | Verser et al. | |
| 7,601,865 B2 | 10/2009 | Verser et al. | |
| 7,682,812 B2 | 3/2010 | Verser et al. | |
| 7,803,969 B2 | 9/2010 | Nordhoff et al. | |
| 7,842,844 B2 | 11/2010 | Atkins | |
| 7,851,397 B2 | 12/2010 | Liang et al. | |
| 7,884,253 B2 | 2/2011 | Stites et al. | |
| 7,888,082 B2 | 2/2011 | Verser et al. | |

(Continued)

FOREIGN PATENT DOCUMENTS

| | | |
|---|---|---|
| DE | 2145049 | 3/1973 |
| DE | 10336386 | 3/2004 |

(Continued)

OTHER PUBLICATIONS

M. Ai., Applied Catalysis, 36, pp. 221-230 (1988).
M. Ai., Applied Catalysis, 48, pp. 51-61 (1989).
M. Ai., Applied Catalysis, 54, 1989, pp. 29-36.
M. Ai., Applied Catalysis, 252, 2003, pp. 185-191.
M. Ai., Journal of Catalysis, 107, 1987, pp. 201-208.
M. Ai., Journal of Catalysis, 124, 1990, pp. 293-296.
M. Ai., Shokubai, 29, 522 (1987), www.shokubai.org/jnl/cgi-bin/ccotw.cgi.
Bosman, et al., Journal of Catalysis, vol. 148, p. 660 (1994).
Brinker C J & Scherer G W, "Sol-Gel Science" published by Academic Press (1990).

(Continued)

*Primary Examiner* — Yong Chu

(57) ABSTRACT

The invention relates to a process for producing an acrylate product comprising the step of reacting a reaction gas mixture A comprising methanol and oxygen to form a product gas mixture A. The process may further comprise the step of combining at least a portion of the product gas mixture A and acetic acid to form a reaction gas mixture B. The process may further comprise the step of reacting at least a portion of the acetic acid in the reaction gas input mixture B with at least a portion of the formaldehyde in the reaction gas input mixture B to form a product gas mixture B. The process may further comprise the step of separating at least a portion of the product gas mixture B to form an alkylenating agent stream comprising at least 1 wt % alkylenating agent and an intermediate acrylate product stream comprising acrylate product.

19 Claims, 3 Drawing Sheets

(56) References Cited

U.S. PATENT DOCUMENTS

| | | |
|---|---|---|
| 7,897,812 B2 | 3/2011 | Machhammer et al. |
| 7,935,850 B2 | 5/2011 | Caers et al. |
| 7,939,597 B2 | 5/2011 | Bub et al. |
| 8,083,815 B2 | 12/2011 | Van Den Berg et al. |
| 8,258,249 B2 | 9/2012 | Bub et al. |
| 8,299,132 B2 | 10/2012 | Gracey et al. |
| 8,299,133 B2 | 10/2012 | Gracey et al. |
| 8,329,960 B2 | 12/2012 | Gracey et al. |
| 8,378,153 B2 | 2/2013 | Daniel et al. |
| 2003/0233012 A1 | 12/2003 | Jackson et al. |
| 2005/0209469 A1 | 9/2005 | Shutt et al. |
| 2005/0261522 A1 | 11/2005 | Isaguliants et al. |
| 2007/0276157 A1 | 11/2007 | Machhammer et al. |
| 2007/0282133 A1 | 12/2007 | Caers et al. |
| 2007/0282134 A1 | 12/2007 | Caers et al. |
| 2008/0193989 A1 | 8/2008 | Verser et al. |
| 2009/0048354 A1 | 2/2009 | Bell et al. |
| 2009/0126259 A1 | 5/2009 | Den Berg et al. |
| 2009/0170963 A1 | 7/2009 | Atkins |
| 2009/0239995 A1 | 9/2009 | Bub et al. |
| 2009/0246111 A1 | 10/2009 | Kato et al. |
| 2009/0281354 A1 | 11/2009 | Mariansky et al. |
| 2009/0292148 A1 | 11/2009 | Gracey et al. |
| 2010/0016454 A1 | 1/2010 | Gracey et al. |
| 2011/0004034 A1 | 1/2011 | Daniel et al. |
| 2011/0071311 A1 | 3/2011 | Johnson et al. |
| 2011/0144294 A1 | 6/2011 | Bub et al. |
| 2011/0224462 A1 | 9/2011 | Ditzel et al. |
| 2011/0237689 A1 | 9/2011 | Bae et al. |
| 2012/0071687 A1 | 3/2012 | Herzog et al. |
| 2012/0071688 A1* | 3/2012 | Herzog et al. ............... 562/599 |

FOREIGN PATENT DOCUMENTS

| | | |
|---|---|---|
| EP | 1904426 | 4/2008 |
| EP | 1967507 | 9/2008 |
| EP | 2060553 | 5/2009 |
| EP | 2072486 | 6/2009 |
| EP | 2072487 | 6/2009 |
| EP | 2072488 | 6/2009 |
| EP | 2072490 | 6/2009 |
| EP | 2072492 | 6/2009 |

OTHER PUBLICATIONS

Iler R K, The Chemistry of Silica, (Wiley, New York, 1979).
Jubb & Bowen, Journal of Material Science, vol. 22, pp. 1963-1970 (1987).
Monros, et al., Journal of Material Science, vol. 28, p. 5832 (1993).

* cited by examiner

INTEGRATED PROCESS FOR THE PRODUCTION OF ACRYLIC ACIDS AND ACRYLATES

FIELD OF THE INVENTION

The present invention relates generally to the production of acrylic acid via a process that integrates a methanol oxidation reaction zone, an aldol condensation reaction zone, and a separation zone.

BACKGROUND OF THE INVENTION

The present invention relates to a process for preparing acrylic acid from methanol and acetic acid. The present invention also relates to the preparation of conversion products from acrylic acid thus obtained.

α,β-unsaturated acids, particularly acrylic acid and methacrylic acid, and the ester derivatives thereof are useful organic compounds in the chemical industry. These acids and esters are known to readily polymerize or co-polymerize to form homopolymers or copolymers. Often the polymerized acids are useful in applications such as superabsorbents, dispersants, flocculants, and thickeners. The polymerized ester derivatives are used in coatings (including latex paints), textiles, adhesives, plastics, fibers, and synthetic resins.

Because acrylic acid and its esters have long been valued commercially, many methods of production have been developed. One exemplary acrylic acid ester production process utilizes: (1) the reaction of acetylene with water and carbon monoxide; and/or (2) the reaction of an alcohol and carbon monoxide, in the presence of an acid, e.g., hydrochloric acid, and nickel tetracarbonyl, to yield a crude product comprising the acrylate ester as well as hydrogen and nickel chloride. Another conventional process involves the reaction of ketene (often obtained by the pyrolysis of acetone or acetic acid) with formaldehyde, which yields a crude product comprising acrylic acid and either water (when acetic acid is used as a pyrolysis reactant) or methane (when acetone is used as a pyrolysis reactant). These processes have become obsolete for economic, environmental, or other reasons.

More recent acrylic acid production processes have relied on the gas phase oxidation of propylene, via acrolein, to form acrylic acid. The reaction can be carried out in single- or two-step processes but the latter is favored because of higher yields (see, for example, DE-A 103 36 386). The oxidation of propylene produces acrolein, acrylic acid, acetaldehyde and carbon oxides. Acrylic acid from the primary oxidation can be recovered while the acrolein is fed to a second step to yield the crude acrylic acid product, which comprises acrylic acid, water, small amounts of acetic acid, as well as impurities such as furfural, acrolein, and propionic acid. Purification of the crude product may be carried out by azeotropic distillation. Although this process may show some improvement over earlier processes, this process suffers from production and/or separation inefficiencies. In addition, this oxidation reaction is highly exothermic and, as such, creates an explosion risk. As a result, more expensive reactor design and metallurgy are required.

Propylene can be produced from mineral oil with comparatively low production costs. In view of the foreseeable shortage in the fossil resource of mineral oil, however, there may be a need for processes for preparing acrylic acid from other raw materials.

WO 2005/093010 proposes the use of the two-stage heterogeneously catalyzed partial gas phase oxidation of propylene to acrylic acid. The propylene may be obtained from methanol. The advantage of such a procedure is that methanol is obtainable both from base fossil raw materials such as coal, for example brown coal and hard coal as disclosed in WO 2010/072424, and/or natural gas, as disclosed in WO 2010/067945. Both of these sources have a much longer lifetime than mineral oil. A disadvantage of the procedure proposed in WO 2005/093010, however, is that the selectivity to propylene based on methanol converted is less than 70 mol %, which is unsatisfactory (in addition to propylene, for example, ethylene and butylene are also formed).

WO 2008/023040, for example, has disclosed the preparation of acrylic acid and the conversion products thereof starting from glycerol, a renewable raw material. A disadvantage of such a procedure, however, is that glycerol is only feasibly obtainable as a renewable raw material essentially as a coproduct of biodiesel production. And the current energy balance of biodiesel production is unsatisfactory.

Some references, for example, DE-A 102006024901, have disclosed the preparation of acrylic acid from propane, which is a raw constituent of natural gas. A disadvantage of such a method, however, is that propane is generally high unreactive.

The aldol condensation reaction of formaldehyde and acetic acid and/or carboxylic acid esters has been disclosed in literature. This reaction forms acrylic acid and is often conducted over a catalyst. For example, condensation catalysts consisting of mixed oxides of vanadium and phosphorus were investigated and described in M. Ai, *J. Catal.*, 107, 201 (1987); M. Ai, *J. Catal.*, 124, 293 (1990); M. Ai, *Appl. Catal.*, 36, 221 (1988); and M. Ai, *Shokubai*, 29, 522 (1987).

U.S. Patent Publication No. 2012/0071688 discloses a process for preparing acrylic acid from methanol and acetic acid in which the methanol is partially oxidized to formaldehyde in a heterogeneously catalyzed gas phase reaction. The product gas mixture thus obtained and an acetic acid source are used to obtain a reaction gas input mixture that comprises acetic acid and formaldehyde. The acetic acid is used in excess over the formaldehyde. The formaldehyde present in reaction gas input mixture is aldol-condensed with the acetic acid via heterogeneous catalysis to form acrylic acid. Unconverted acetic acid still present alongside the acrylic acid in the product gas mixture is removed therefrom and is recycled to the reaction gas input mixture. Although US Patent Publication No. 2012/0071688 may disclose many details related to methanol oxidation and aldol condensation reactions, the reference discloses very little about the separation schemes necessary to effectively separate the crude condensation product mixtures.

Although the methanol oxidation reaction and the aldol condensation reaction are disclosed, there has been little if any disclosure relating to separation schemes that may be employed to effectively provide purified acrylic acid from the aldol condensation crude product, which contains significant amounts of formaldehyde, which is known to cause problems in the purification of acrylate products.

Thus, the need exists for a process for producing purified acrylate product, e.g., acrylic acid, which provides for efficient separation of purified acrylate product from the crude aldol condensation product.

The references mentioned above are hereby incorporated by reference.

BRIEF DESCRIPTION OF DRAWINGS

The invention is described in detail below with reference to the appended drawings, wherein like numerals designate similar parts.

SUMMARY OF THE INVENTION

Figure 1:
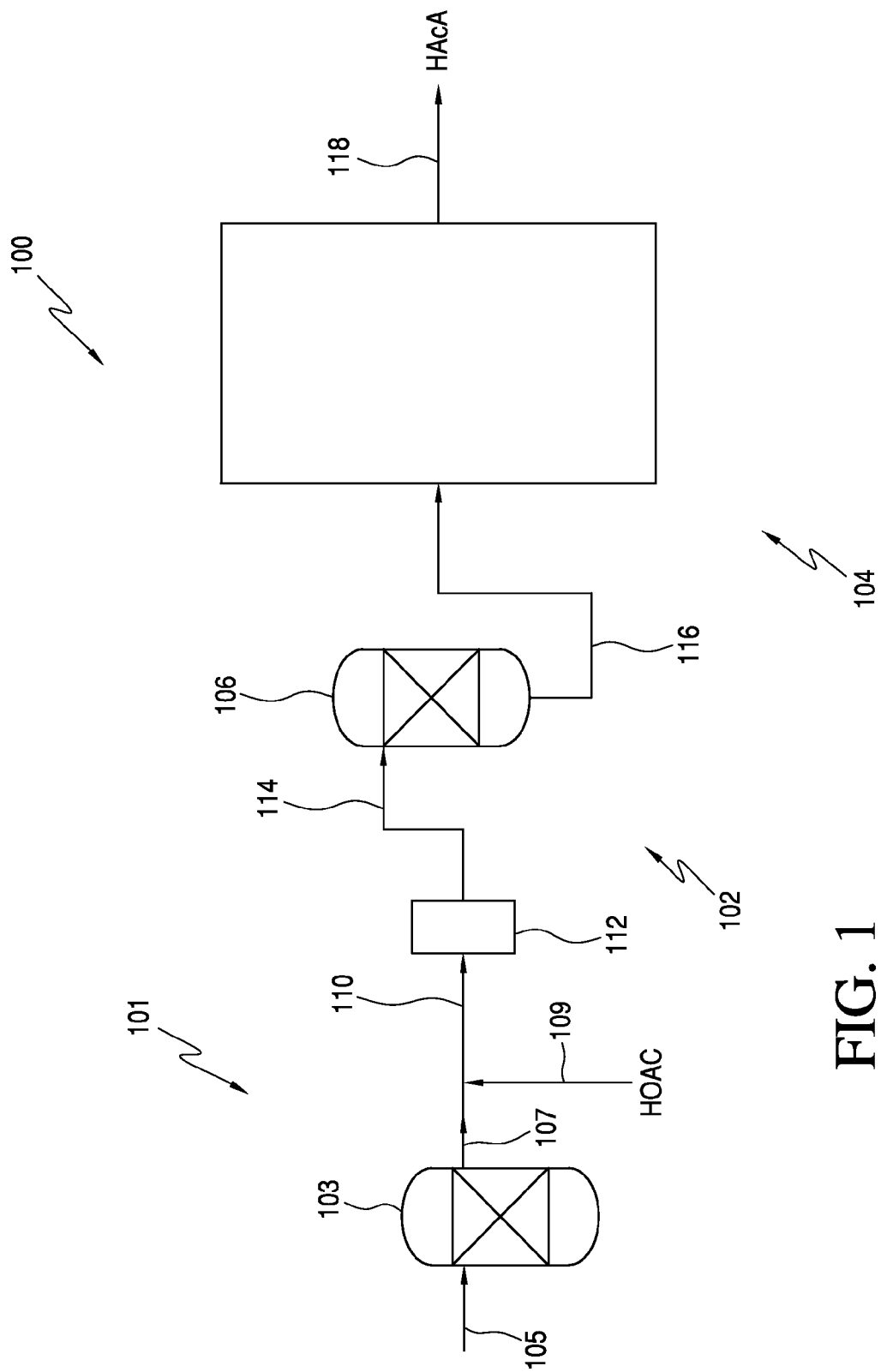
FIG. 1 is a schematic of an acrylic acid reaction/separation system in accordance with an embodiment of the present invention.

In one embodiment, the invention relates to a process for producing an acrylate product. The process comprises the step of reacting a reaction gas mixture A comprising methanol, oxygen, and at least one diluent gas other than steam to form a product gas mixture A. The product gas mixture A may comprise formaldehyde, steam, and at least one inert diluent gas other than steam. The reaction may be conducted in a first reaction zone. The process may further comprise the step of combining at least a portion of the product gas mixture A and acetic acid to form a reaction gas mixture B. The reaction gas mixture B may comprise acetic acid, formaldehyde, steam, and at least one diluent gas other than steam. The process may further comprise the step of reacting at least a portion of the acetic acid in the reaction gas input mixture B with at least a portion of the formaldehyde in the reaction gas input mixture B to form a product gas mixture B. The product gas mixture B may comprise acrylic acid, acetic acid, steam, and at least one inert diluent gas other than steam. The reaction may be conducted in a second reaction zone. The process may further comprise the step of separating at least a portion of the product gas mixture B to form an alkylenating agent stream comprising at least 1 wt % alkylenating agent and an intermediate acrylate product stream comprising acrylate product.

DETAILED DESCRIPTION OF THE INVENTION

Introduction

Production of unsaturated carboxylic acids such as acrylic acid and methacrylic acid and the ester derivatives thereof via most conventional processes have been limited by economic and environmental constraints. In the interest of finding a new reaction path, the aldol condensation reaction of acetic acid and formaldehyde has been investigated. The formaldehyde may be formed via the oxidation of methanol. This aldol condensation reaction may yield a unique crude product that comprises, inter alia, a higher amount of (residual) formaldehyde, which is generally known to add unpredictability and problems to separation schemes. Although the aldol condensation reaction of acetic acid and formaldehyde is known, there has been little if any disclosure relating to separation schemes that may be employed to effectively provide purified acrylic acid from the aldol condensation crude product.

A process for preparing acrylic acid from methanol is provided herein. In contrast to the process of WO 2005/093010, which is also based on the raw material methanol, the process according to the invention possesses an increased selectivity of acrylic acid formation based on the amount of methanol converted.

One benefit demonstrated by the embodiments of the present invention is that the acetic acid is itself obtainable in a simple and industrially tried and tested manner proceeding from methanol, by carbonylation thereof with carbon monoxide (see, for example, Industrielle Organische Chemie [Industrial Organic Chemistry], Klaus Weissermel and Hans-Jurgen Arpe, Wiley-VCH, Weinheim, 5th edition (1998), p. 194 to 198).

In this document, base fossil raw materials shall be understood to mean base raw materials which, like brown coal, hard coal, natural gas and mineral oil, for example, are Banned from degradation products of dead plants and dead animals.

In contrast, in this document, renewable raw materials shall be understood to mean those raw materials which are obtained from fresh biomass, e.g., from (new) vegetable and animal material which is being newly grown (in the present) and will be grown in the future.

One advantage of an acrylic acid preparation process based on the raw material methanol is that the methanol can be obtained via synthesis gas (gas mixtures of carbon monoxide and molecular hydrogen) in principle from all carbonaceous base fossil materials and all carbonaceous renewable raw materials. As in the case of methane, the molecular hydrogen required may already be present in the carbon carrier (a process for obtaining methane from biogas or biomass is described, for example, in DE-A 102008060310 and EP-A 2220004). An alternative hydrogen source is water, from which molecular hydrogen can be obtained, for example, by means of electrolysis. The oxygen source is generally air (see, for example, WO 10-060236 and WO 10-060279). A suitable renewable carbonaceous raw material for synthesis gas production is, for example, lignocellulose (see, for example, WO 10-062936). It is also possible to obtain synthesis gas by coupling the pyrolysis of biomass directly with steam reforming.

The present invention thus provides a process for preparing acrylic acid from methanol and acetic acid, which comprises the following measures. A stream of a reaction gas input mixture A comprising the methanol and molecular oxygen reactants and at least one inert diluent gas other than steam is directed through a first reaction zone A, which is charged with at least one oxidation catalyst A. The reaction gas input mixture may comprise oxygen and methanol, preferably in a molar ratio of at least 1, e.g., at least 2, at least 5, or at least 10. In the course of passage through reaction zone A, methanol present in the reaction gas input mixture A is oxidized under heterogeneous catalysis to form formaldehyde and steam, which exit as product gas mixture A. Product gas mixture A comprises formaldehyde, steam, and at least one inert diluent gas other than steam. The oxidation reaction may, in some embodiments, be conducted with or without excess molecular oxygen. Product gas mixture A leaves reaction zone A. In one embodiment, molecular oxygen and/or further inert diluent gas other than steam are supplied to the reaction gas mixture A flowing through reaction zone A. Product gas mixture A may, in some embodiments, comprise methanol, e.g., unconverted methanol. Optionally, the stream of product gas mixture A leaving reaction zone A may be fed to a separation zone T* and any unconverted methanol still present in product gas mixture A in separation zone T* may be removed from product gas mixture A to leave a formaldehyde-comprising product gas mixture A*. A stream of product gas mixture A* leaves reaction zone A. The process may form a stream of a reaction gas input mixture B from the product gas mixture A. The reaction gas input mixture B may comprise acetic acid, steam, at least one inert diluent gas other than steam, and formaldehyde, with or without molecular oxygen. In one embodiment, the molar amount of acetic acid, $n_{HAc}$, present in the reaction gas input mixture B is greater than the molar amount of formaldehyde, $n_{Fd}$, present in the reaction gas input mixture B. The reaction gas input mixture B may be formed by combining an acetic acid stream and at least a portion of product gas mixture A.

The reaction gas input mixture B is passed through a second reaction zone B, which is charged with at least one aldol condensation catalyst B. Formaldehyde present in reaction gas input mixture B, as it flows through reaction zone B, is condensed with acetic acid present in reaction gas input mixture B (preferably under heterogeneous catalysis) to form product gas mixture B comprising acrylic acid and water. In one embodiment, the reaction gas mixture B comprises acetic acid and formaldehyde in a molar ratio ranging from 1 to 10, e.g., from 1 to 8 or from 1 to 5. Product gas mixture B comprises acrylic acid, acetic acid, steam and at least one inert diluent gas other than steam, optionally with or without molecular oxygen. The product gas mixture B leaves reaction zone B. In one embodiment, it optionally is possible to supply further molecular oxygen and/or further inert diluent gas to the reaction gas mixture B. The stream of product gas mixture B leaving reaction zone B is fed to a separation zone T and separated in separation zone T into at least three streams X, Y and Z. The acrylic acid flow present in stream X is greater than the acrylic acid flow present in streams Y and Z together. The acetic acid flow present in stream Y is greater than the acetic acid flow present in streams X and Z together. The flow of inert diluent gas other than steam present in stream Z is greater than the flow of inert diluent gas other than steam present in streams X and Y together. Stream Y may be recycled into reaction zone B and used to obtain reaction gas input mixture B.

A significant advantage of the inventive procedure is that the formaldehyde present in product gas mixture A need not be removed from product gas mixture A in order to be able to use it to obtain reaction gas input mixture B.

Instead, the formaldehyde-comprising stream of product gas mixture A leaving reaction zone A can be used as such, e.g., without conducting a removal process thereon beforehand, in order to obtain the reaction gas input mixture B. In general, for this purpose, the product gas mixture A will first be cooled (quenched) when it leaves reaction zone A in order to reduce unwanted further reactions in product gas mixture A before the introduction thereof into reaction gas input mixture B. Typically, it will be cooled as rapidly as possible to temperatures of 150 to 350° C., or 200 to 250° C.

Optionally, it is also possible to first remove a portion or the entirety of any methanol which has not been converted in reaction zone A and is still present in product gas mixture A from the latter in a separation zone T*, and then to use the remaining formaldehyde-comprising product gas mixture A* (which may pass through the liquid state in the course of the removal) to obtain reaction gas input mixture B. Advantageously, in some embodiments, the removal will be undertaken by rectificative means, e.g., a rectification column. For this purpose, product gas mixture A, optionally after preceding direct or indirect cooling, can be fed in gaseous form to the corresponding rectification column provided with cooling circuits. It is of course possible, however, first to convert those constituents whose boiling point at standard pressure ($10^5$ Pa) is less than or equal to the boiling point of formaldehyde from product gas mixture A to the liquid phase (for example by condensation), and to undertake the rectification from the liquid phase. In general, such a methanol removal may also be accompanied by a removal of steam present in product gas mixture A. For the purpose of the aforementioned direct cooling, it is possible to use, for example, a liquid phase which has been withdrawn from the bottom region of the rectification column and has optionally additionally been cooled by indirect heat exchange, which is sprayed by means of appropriate nozzles into fine droplets which provide the large heat exchange area required for the hot product gas mixture A. Appropriately, in accordance with the invention, the methanol removed may be recycled into reaction zone A and used to obtain the reaction gas input mixture A. Removal of methanol from product gas mixture A, prior to its use in forming reaction gas input mixture B, is generally utilized when reaction zone A is configured such that the resulting conversion of methanol in reaction zone A, based on the single pass of product gas mixture A through reaction zone A, is not more than 90 mol %. It will be appreciated that such a methanol removal, however, can also be employed in the case of corresponding methanol conversions of not more than 95 mol %. For example, such a methanol removal can be undertaken as described in Ullmann's Encyclopedia of Industrial Chemistry, vol. A11, 5th ed., VCH Weinheim.

The oxidation catalysts A particularly suitable for charging of reaction zone A can be divided essentially into two groups.

The first of the two groups comprises silver catalysts, which have, as the active material, elemental silver whose purity is preferably ≥99.7% by weight, advantageously ≥99.8% by weight, preferably ≥99.9% by weight and most preferably ≥99.99% by weight. The corresponding processes for heterogeneously catalyzed partial gas phase oxidation of methanol to formaldehyde over these "silver catalysts" are described as silver processes (see, for example, "A. Nagy, G. Mestl: High temperature partial oxidation reactions over silver catalysts, Appl. Catal. 188 (1999), p. 337 to 353", "H. Schubert, U. Tegtmayr, R. Schlogl: On the mechanism of the selective oxidation of methanol over elemental silver, Catalyst Letters, 28 (1994), p. 383 to 395", "L. Lefferts, Factors controlling the selectivity of silver catalysts for methanol oxidation, thesis, University of Twente (1987)" and DE-A 2334981).

Silver oxidation catalysts A advantageous in accordance with the invention for charging of reaction zone A are disclosed, for example, in Ullmann's Encyclopedia of Industrial Chemistry, vol. A11, 5th ed., VCH, Weinheim, or in Encyclopedia of Chemical Technology, vol. 11, 4th ed., Wiley & Sons, New York, p. 929 to 949, in DE-B 1231229, in DE-B 1294360, in DE-A 1903197 and in BE patent 683130. Typically, these comprise crystals (the shape of which may also be round) of elemental silver (preferably of the abovementioned purity) which have been deposited by electrolysis of aqueous silver salt solutions and which can be poured as a fixed catalyst bed onto a perforated base (for example a perforated plate, a sieve or a mesh network (preferably likewise manufactured from silver)) (typical bed heights are 10 to 50 mm, frequently 15 to 30 mm). The total content of metals present in elemental form other than silver in the catalytically active silver (e.g. Cu, Pd, Pb, Bi, Fe, Pt and Au) is advantageously ≥30 ppm by weight, better ≥50 ppm by weight, preferably ≥100 ppm by weight and more preferably ≥1000 ppm by weight or ≥2000 ppm by weight. The longest dimension of the silver crystals is typically in the range from 0.1 to 5 mm and preferably increases in flow direction of reaction gas mixture A. The fixed silver bed is preferably configured as a two-layer bed, in which case the lower layer has a thickness, for example, of 15 to 40 mm, preferably 20 to 30 mm, and consists to an extent of at least 50% by weight of silver crystals of particle size 1 to 4 mm, preferably 1 to 2.5 mm. The upper layer may have, for example, a thickness (layer thickness) of 0.75 to 3 mm, preferably 1 to 2 mm, and consist of crystals having particle sizes (longest dimensions) of 0.1 to 1 mm, preferably 0.2 to 0.75 mm. In this case, reaction gas input mixture A flows in from the top downward.

In order to counteract sintering of the silver crystals with increasing operating time (at comparatively high reaction temperatures), which reduces the performance of the fixed catalyst bed, it is recommended to coat the silver crystals with a thin porous layer of oxidic material of at least one of the elements Al, Si, Zr and Ti (the layer thickness may be 0.3 to 10 μm, preferably 1.0 to 5.0 more preferably 2.0 to 4.0 μm and at best about 3 μm), and in this way achieving prolonging of the service life of the fixed catalyst bed.

The methanol content in reaction gas input mixture A is, in the silver process, normally at least 5% by volume, usually at least 10% by volume, and may extend up to 60% by volume. The aforementioned methanol content in the silver process is preferably 15 to 50% by volume and more preferably 20 to 40 or to 30% by volume.

In addition, the ratio of the molar amount of molecular oxygen present in reaction gas input mixture A ($n_o$) to the molar amount of methanol present in reaction gas input mixture A ($n_{Me}$), $n_o:n_{Me}$, in the silver process is normally less than 1 (<1), preferably ≤0.8. It will more preferably range from 0.2 to 0.6 and most preferably 0.3 to 0.5 or 0.4 to 0.5. In one embodiment, $n_o:n_{me}$ in the silver process is not less than 0.1.

In this document, an inert diluent gas shall be understood to mean a reaction gas input mixture constituent which behaves inertly under the conditions in the respective reaction zone A and/or B and, viewing each inert reaction gas constituent individually, remains chemically unchanged in the particular reaction zone to an extent of more than 95 mol %, preferably to an extent of more than 97 mol %, or to an extent of more than 98 mol %, or to an extent of more than 99 mol %.

Examples of inert diluent gases both for reaction zone A and reaction zone B are water, $CO_2$, $N_2$ and noble gases such as Ar, and mixtures of the aforementioned gases. One task assumed by the inert diluent gases is that of absorbing heat of reaction released in the reaction zone A, thus limiting what is called the hotspot temperature in reaction zone A and having a favorable effect on the ignition behavior of reaction gas mixture A. The hotspot temperature is understood to mean the highest temperature of reaction gas mixture A on its way through reaction zone A.

A preferred inert diluent gas other than steam in the case of the silver process for reaction gas input mixture A is molecular nitrogen. The advantage thereof may be based on the fact that molecular nitrogen occurs in air as a natural companion of molecular oxygen, which makes air a preferred source of the molecular oxygen required in reaction zone A. It will be appreciated that, in the case of the silver process, it is, however, also possible in accordance with the invention to use pure molecular oxygen, or air enriched with molecular oxygen, or another mixture of molecular oxygen and inert diluent gas, as the oxygen source.

Typically, reaction gas input mixture A comprises, in the case of the silver process, 20 to 80% by volume, or 30 to 70% by volume, or 40 to 60% by volume, of inert diluent gas. The latter may be entirely free of steam. In some embodiments, reaction gas input mixture A in the case of the silver process may comprise 20 to 80% by volume, or 30 to 70% by volume, or 40 to 60% by volume, of molecular nitrogen. In principle, reaction gas input mixture A in the case of the silver process may comprise >0 to 50% by volume of water.

Steam is advantageous as a constituent of reaction gas input mixture A in that steam, compared to $N_2$ and noble gases for example, has an increased molar heat capacity. In general, steam as a constituent of reaction gas mixture A is also beneficial for the desorption of the desired partial oxidation product from the catalyst surface, which has a positive effect on the selectivity of the desired product formation. Since presence of steam in reaction zone B, however, generally reduces the desired aldol condensation to a certain extent and also increases the energy expenditure required to remove a stream X comprising enriched acrylic acid from product gas mixture B in separation zone T (acrylic acid has an elevated affinity for water), appropriately in accordance with the invention, comparatively limited steam contents of reaction gas input mixture A are preferred.

In one embodiment, reaction gas input mixture A in the silver process preferably comprises from 5 to 45% by volume of water, advantageously from 10 to 40% by volume and particularly advantageously from 15 to 35% by volume, or from 20 to 30% by volume of water. The boiling point of the inert diluent gases other than steam (based on a pressure of $10^5$ Pa=1 bar) is normally well below that of steam (based on the same pressure), and therefore stream Z in the process according to the invention generally comprises the inert diluent gases other than steam, e.g., $N_2$ and $CO_2$ in enriched form. Advantageously in some embodiments, the separation of product gas mixture B in separation zone T will be performed in such a way that stream Z also has an appropriate content of steam. In the latter case, stream Z may function both as a source for inert gases other than steam and for steam. The inert gas source used in the silver process for reaction gas input mixture A may thus also be the stream Z obtained in separation zone T. Appropriately in one embodiment, in the silver process, a substream of stream Z will be recycled into reaction zone A to obtain reaction gas input mixture A (cycle gas method). It will be appreciated that a portion of stream Z may also be recycled into reaction zone B.

In some embodiments, suitable reaction gas input mixtures A may, in the silver process, comprise, for example, 10 to 50% by volume of water and 20 to 60% by volume of inert diluent gas other than steam (e.g. $N_2$, or $N_2+CO_2$, or $N_2$+noble gas (e.g. Ar), or $N_2+CO_2$+noble gas (e.g. Ar)).

It will be appreciated that reaction gas input mixtures A in the silver process may also comprise 10 to 40% by volume of water and 30 to 60% by volume of inert diluent gases other than steam (for example those mentioned above).

Of course, reaction gas input mixture A, in the silver process, may also comprise 20 to 40% by volume of water and 30 to 50% by volume of inert diluent gases other than steam (for example those mentioned above).

In principle, in the case of the silver process, reaction gas mixture A can be either forced or drawn through reaction zone A. Accordingly, the working pressure in the case of the silver process within reaction zone A may be either ≥$10^5$ Pa or <$10^5$ Pa. Appropriately in one embodiment, the working pressure in the case of the silver process in reaction zone A will be $10^3$ to $10^6$ Pa, preferably $10^4$ to $5 \times 10^5$ Pa, more preferably $10^4$ to $2 \times 10^5$ Pa and most preferably $0.5 \times 10^5$ Pa to $1.8 \times 10^5$ Pa.

The temperature of reaction gas mixture A (the term "reaction gas mixture A" comprises, in the present application, all gas mixtures which occur in reaction zone A and are between reaction gas input mixture A and product gas mixture A) will, in the case of the silver process, within reaction zone A, normally be within the range from 400 to 800° C., preferably within the range from 450 to 800° C. and more preferably within the range from 500 to 800° C. The term "temperature of reaction gas mixture A" (also referred to in this document as reaction temperature in reaction zone A) means primarily that temperature which reaction gas mixture A has from attainment of a conversion of the methanol present in reaction gas input mixture A of at least 5 mol % until attainment of the corresponding final conversion of the methanol within reaction zone A.

Advantageously in accordance with the invention, the temperature of reaction gas input mixture A in the case of the silver process is within the aforementioned temperature ranges over the entire reaction zone A.

Advantageously, in the case of the silver process, reaction gas input mixture A is also supplied to reaction zone A already with a temperature within the aforementioned range. Frequently, in the case of the silver process, a charge of reaction zone A with solid inert material or of catalytically active catalyst charge highly diluted with such inert material is present at the inlet into reaction zone A upstream in flow direction of the actually catalytically active catalyst charge (which may also be diluted with inert shaped bodies). As it flows through such an upstream charge of reaction zone A, the temperature of the reaction gas input mixture A supplied to reaction zone A in the case of the silver process can be adjusted comparatively easily to the value with which reaction gas mixture A in the case of the silver process is to enter the actual catalytically active catalyst charge of reaction zone A.

When the temperature of reaction gas mixture A in the case of the silver process within reaction zone A is limited to values of 450 to 650° C., preferably 500 to 600° C., the conversion of methanol will generally be ≤90 mol %, frequently ≤85 mol % or ≤80 mol %, while the selectivity of formaldehyde formation will be at values of ≥90 mol %, in many cases ≥93 mol % or ≥95 mol %. In this case (in which the steam content of the reaction gas input mixture is preferably <10% by volume), it is appropriate in accordance with the invention to remove from product gas mixture A at least a portion of unconverted methanol prior to the use thereof for obtaining reaction gas input mixture B, and to recycle it into the production of reaction gas input mixture A.

Advantageously in accordance with the invention, the temperature of reaction gas mixture A in the case of the silver process within reaction zone A will therefore be 550 to 800° C., preferably 600 to 750° C. and more preferably 650 to 750° C.

At the same time, the steam content of reaction gas input mixture A in the case of the silver process is advantageously adjusted to values of ≥10% by volume, preferably ≥15% by volume and particularly advantageously ≥20% by volume. Both the elevated temperature and the elevated steam content of reaction gas input mixture A, in the case of the silver process, have an advantageous effect on the methanol conversion (based on a single pass of reaction gas mixture A through reaction zone A). In general, this conversion will be >90 mol %, in many cases ≥92 mol %, or ≥95 mol % and frequently even ≥97 mol % (see, for example, Ullmann's Encyclopedia of Industrial Chemistry, vol. A 11, 5th ed., VCH Weinheim). The high methanol conversions which are to be achieved in the case of the silver process in spite of the comparatively low $n_o:n_{me}$ ratios in reaction gas input mixture A are attributable in particular to the fact that, with increasing temperature of reaction gas mixture A in reaction zone A, the exothermic partial oxidation

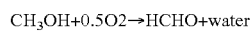

$$CH_3OH + 0.5 O_2 \rightarrow HCHO + \text{water}$$

is increasingly accompanied by the endothermic dehydration

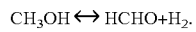

$$CH_3OH \leftrightarrow HCHO + H_2.$$

In this way, in the case of the silver process, it is regularly possible to achieve yields of formaldehyde of ≥85 mol %, usually ≥87 mol % and in many cases ≥89 mol % based on a single pass of reaction gas mixture A through reaction zone A and the molar amount of methanol converted. Otherwise, the silver process can be performed as described in the documents already mentioned in this regard, or as described in documents U.S. Pat. Nos. 4,080,383, 3,994,977, 3,987,107, 4,584,412 and U.S. Pat. No. 4,343,954. It will be appreciated that, in the case of the silver process described, it is possible not only to use comparatively pure methanol as the raw material (source). Methanol raw materials suitable in accordance with the invention in this regard are also aqueous methanol solutions and technical-grade methanol, which can be used after appropriate evaporation to obtain reaction gas input mixture A.

Suitable reactors for execution of the silver process in reaction zone A include not only those recommended in the aforementioned references but also heat exchanger reactors.

A heat exchanger reactor has at least one primary space and at least one secondary space, which are separated from one another by a dividing wall. The catalyst charge positioned in the at least one primary space comprises at least one oxidation catalyst A, and reaction gas mixture A flows through it. At the same time, a fluid heat carrier flows through the secondary space and heat exchange takes place between the two spaces through the dividing wall, which pursues the purpose of monitoring and controlling the temperature of reaction gas mixture A on its way through the catalyst bed (of controlling the temperature of reaction zone A).

Examples of heat exchanger reactors suitable in accordance with the invention for the implementation of reaction zone A are the tube bundle reactor (as disclosed, for example, in EP-A 700714 and the references cited in that document) and the thermoplate reactor (as disclosed, for example, in documents EP-A 1651344, DE-A 10361456, DE-A 102004017150 and the references acknowledged in these documents). In the case of the tube bundle reactor, the catalyst bed through which reaction gas mixture A flows is preferably within the tubes thereof (the primary spaces), and at least one heat carrier is conducted through the space surrounding the reaction tubes (the secondary space). Useful heat carriers for the heat exchanger reactors are, for example, salt melts, heat carrier oils, ionic liquids and steam. In general, tube bundle reactors used on the industrial scale comprise at least three thousand up to several tens of thousands of reaction tubes connected in parallel (reactor tubes). It will be appreciated that the configuration of reaction zone A can also be implemented in a fluidized bed reactor or a micro reactor.

Conventional reactors and micro reactors differ by their characteristic dimensions and especially by the characteristic dimensions of the reaction space which accommodates the catalyst bed through which the reaction gas mixture flows.

The space velocity of methanol present in reaction gas input mixture A on the reactor charged with silver crystals will generally be $(0.5 \text{ to } 6) \times 10^3$ kg of methanol per m² of reactor cross section or cross section of the fixed catalyst bed.

Preferably, in some embodiments, the heterogeneously catalyzed partial gas phase oxidation of methanol to formaldehyde in reaction zone A may be performed by the FORMOX process.

In contrast to the silver process, the FORMOX process is performed over oxidation catalysts A whose active material is a mixed oxide which has at least one transition metal in the oxidized state (see, for example, WO 03/053556 and EP-A 2213370). The term "transition metals" means the chemical elements of the Periodic Table with atomic numbers 21 to 30, 39 to 48 and 57 to 80.

Preferably, in accordance with the invention, aforementioned mixed oxide active materials comprise at least one of the transition metals Mo and V in the oxidized state. Most preferably in accordance with the invention, the aforementioned active materials are mixed oxides having at least the elements Fe and Mo in the oxidized state (see, for example, U.S. Pat. Nos. 3,983,073, 3,978,136, 3,975,302, 3,846,341, 3,716,497, 4,829,042, EP-A 2213370 and WO 2005/063375, U.S. Pat. Nos. 3,408,309, 3,198,753, 3,152,997, WO 2009/1489809, DE-A 2145851, WO 2010/034480, WO 2007/059974 and "Methanol Selective Oxidation to Formaldehyde over Iron-Molybdate Catalysts, Ana Paula Vieira Soares and Manuel Farinha Portela and Alain Kiennemann in Catalysis Review 47, pages 125 to 174 (2004)" and the references cited in these documents).

A further difference between the silver process and the FORMOX process is that the ratio of the molar amount of molecular oxygen present in reaction gas input mixture A ($n_o$) to the molar amount of methanol present in reaction gas input mixture A ($n_{Me}$), $n_o:n_{Me}$, is normally at least 1 or greater than 1 ($\geq 1$), preferably 1.1. In some embodiments, the $n_o:n_{Me}$ ratio in reaction gas input mixture A in the FORMOX process will, however, be not more than 5, frequently not more than 4. $n_o:n_{Me}$ ratios which are advantageous in accordance with the invention in reaction gas input mixture A are 1.5 to 3.5, preferably 2 to 3. An oxygen excess is advantageous in accordance with the invention in that, in the inventive procedure, the oxygen is introduced via product gas mixture A into reaction gas input mixture B, and hence into reaction zone B, which has an advantageous effect on the service life of the aldol condensation catalyst B. In addition, the methanol content of reaction gas input mixture A in the FORMOX process typically may be not more than 15% by volume, usually not more than 11% by volume because gas mixtures of molecular nitrogen, molecular oxygen and methanol with a molecular oxygen content of not more than approximately 11% by volume of molecular oxygen are outside the explosion range. In some embodiments, the methanol content in reaction gas input mixture A in the case of the FORMOX process will be 2% by volume, preferably 4 to 10% by volume and more preferably 6 to 9% by volume or 5 to 7% by volume. Gas mixtures of molecular nitrogen, molecular oxygen and methanol whose methanol content is $\leq 6.7\%$ by volume are, irrespective of the molecular oxygen content therein, outside the explosion range, which is why particularly high $n_o:n_{me}$ ratios in reaction gas input mixture A can be employed within this concentration range.

The FORMOX process also differs from the silver process in that the methanol conversions achieved by this process, based on a single pass of reaction gas mixture A through reaction zone A, essentially irrespective of the inert diluent gas used in reaction gas input mixture A, are regularly >90 mol %, typically $\geq 92$ mol %, usually $\geq 95$ mol % and in many cases even $\geq 97$ mol % or $\geq 98$ mol %, or $\geq 99$ mol %. The accompanying selectivities of formaldehyde formation are regularly $\geq 90$ mol %, usually $\geq 92$ mol % and in many cases $\geq 94$ mol %, and frequently even $\geq 96$ mol %.

According to the invention, useful inert diluent gases in reaction gas input mixture A for the FORMOX process (and for the silver process) in reaction zone A are likewise gases such as water, $N_2$, $CO_2$ and noble gases such as Ar, and mixtures of aforementioned gases. A preferred inert diluent gas other than steam in the case of the FORMOX process too in reaction gas input mixture A is molecular nitrogen.

The inert diluent gas content in reaction gas input mixture A may, in the case of the FORMOX process, be 70 to 95% by volume, frequently 70 to 90% by volume and advantageously 70 to 85% by volume. In other words, the molecular nitrogen content of reaction gas input mixture A may, in the case of employment of the FORMOX process, in reaction gas input mixture A, be 70 to 95% by volume, or 70 to 90% by volume, or 70 to 85% by volume. Advantageously in accordance with the invention, reaction gas input mixture A in the case of the FORMOX process may be free of steam. Appropriately in application terms, reaction gas input mixture A, in the case of employment of a FORMOX process in reaction zone A, may have a low steam content for the same reasons as in the case of the silver process. In general, the steam content of reaction gas input mixture A in the FORMOX process in reaction zone A is $\geq 0.1\%$ by volume and $\leq 20\%$ by volume or $\leq 10\%$ by volume, advantageously $\geq 0.2\%$ by volume and $\leq 7\%$ by volume, preferably $\geq 0.5\%$ by volume and $\leq 5\%$ by volume.

A further advantage of the employment of a FORMOX process in reaction zone A, in accordance with the invention, results from the fact that the high methanol conversions described are established at significantly lower reaction temperatures compared to the use of a silver process.

The temperature of reaction gas mixture A in the case of the FORMOX process in reaction zone A will normally be in the range from 250 to 500° C. preferably in the range from 300 to 450° C. and frequently within the range from 270 to 400° C. The meaning of the term "temperature of reaction gas mixture A" corresponds in the case of the FORMOX process to that which has already been given in this document for the silver process.

Advantageously in accordance with the invention, the temperature of reaction gas mixture A (also referred to in this document as the reaction temperature in reaction zone A) in the case of the FORMOX process, over the entire reaction zone A, is within the aforementioned temperature ranges. Advantageously, in the case of the FORMOX process too, reaction gas input mixture A is supplied to reaction zone A already with a temperature within the aforementioned range. Frequently, in the case of the FORMOX process, a charge of reaction zone A with solid inert material or of catalytically active catalyst charge highly diluted with such inert material is present at the inlet into reaction zone A upstream in flow direction of the actual catalytically active catalyst charge (which may also be diluted with inert shaped bodies). As it flows through such an upstream charge of reaction zone A, the temperature of reaction gas input mixture A supplied to reaction zone A in the FORMOX process can be adjusted in a comparatively simple manner to the value with which reaction gas mixture A in the FORMOX process is to enter the actual catalytically active catalyst charge of reaction zone A.

With regard to the working pressure in reaction zone A, the statements made with respect to the silver process may apply correspondingly to the FORMOX process.

Mixed oxide active materials particularly suitable for the FORMOX process are those of the general formula I

$$[Fe_2(MoO_4)_3]_1[M^1{}_mO_n]_q \qquad (I)$$

in which the variables are each defined as follows:
$M^1$ is Mo and/or Fe, or
Mo and/or Fe and a total molar amount, of up to 10 mol % (e.g. 0.01 to 10 mol %, or 0.1 to 10 mol %), preferably not more than 5 mol %, of one or more elements from the group consisting of Ti, Sb, Sn, Ni, Cr, Ce, Al, Ca, Mg, V, Nb, Ag, Mn, Cu, Co, Si, Na, K, Tl, Zr, W, Ir, Ta, As, P and B,
q is 0 to 5, or 0.5 to 3, or 1 to 2,
m is 1 to 3, and
n is 1 to 6, with the proviso that the contents of both sets of square brackets in Formula I are electrically uncharged, e.g., they do not have any electrical charge.

Advantageously, in accordance with the invention, mixed oxide active materials of formula I comprise less than 50 mol %, more preferably less than 20 mol % and more preferably less than 10 mol % of the Fe present in the mixed oxide active material of formula I in the +2 oxidation state, and the remaining amount of the Fe present therein in each case in the +3 oxidation state. Most preferably, the mixed oxide active material of formula I comprises all of the Fe present therein in the +3 oxidation state.

The $n_{mo}:n_{Fe}$ ratio of molar amount of Mo present in a mixed oxide active material of formula I ($n_{mo}$) to molar amount of Fe present in the same mixed oxide active material ($n_{Fe}$) is preferably 1:1 to 5:1.

In addition, it is advantageous in accordance with the invention when $M^1$=Mo and m=1 and n=3. Mixed oxide active materials advantageous in accordance with the invention also exist when $M^1$=Fe and m=2 and n=3.

Favorable mixed oxide active materials of formula I favorable are also those with such a stoichiometry that they can be considered (represented) in a formal sense as a mixture of $MoO_3$ and $Fe_2O_3$, and the $MoO_3$ content of the mixture is 65 to 95% by weight and the $Fe_2O_3$ content of the mixture is 5 to 35% by weight.

Mixed oxide active materials of formula I can be prepared as described in the reference documents cited.

In general, the procedure will be to obtain, from sources of the catalytically active oxide material I, a very intimate, preferably finely divided, dry mixture of composition corresponding to the stoichiometry of the desired oxide material I (a precursor material), and to calcine (thermally treat) it at temperatures of 300 to 600° C. preferably 400 to 550° C. The calcination can be performed either under inert gas or under an oxidative atmosphere, for example air (or another mixture of inert gas and oxygen), or else under a reducing atmosphere (for example a mixture of inert gas and reducing gases such as $NH_3$ and CO). The calcination time will generally be a few hours and typically decreases with the magnitude of the calcination temperature.

Useful sources for the elemental constituents of the mixed oxide active materials I are especially those compounds which are already oxides and/or those compounds which can be converted to oxides by heating, at least in the presence of oxygen. The intimate mixing of the starting compounds (sources) can be performed in dry or in wet form. Where it is performed in dry form, the starting compounds are appropriately used in the form of fine powders and, after mixing and optional compaction, subjected to calcination. However, preference is given to performing the intimate mixing in wet form. In this case, the starting compounds are typically mixed with one another in the form of aqueous suspensions and/or solutions. Particularly intimate dry mixtures are obtained in the mixing process described when the starting materials are exclusively sources of the elemental constituents present in dissolved form.

The solvent used is preferably water. Preference is given to preparing, from the starting compounds, at least two aqueous solutions, at least one of which is an acidic solution and at least one of which is an ammoniacal (basic) solution.

Combination of the aqueous solutions generally results in precipitation reactions in which precursor compounds of the multimetal oxide active material I form.

Subsequently, the aqueous material obtained is dried, and the drying operation can be effected, for example, by spray drying.

The catalytically active oxide material obtained after the calcining of the dry material can be used to charge reaction zone A for the FORMOX process in finely divided form as such, or applied with the aid of a liquid binder to an outer surface of a shaped support body in the form of an eggshell catalyst. However, eggshell catalysts can also be produced by applying, with the aid of a liquid binder, fine precursor powder to the outer surface of shaped support bodies, and calcining the precursor substance only after completion of application and drying.

The multimetal oxide active materials of formula I can, however, also be used in reaction zone A in pure, undiluted form, or diluted with oxidic, essentially inert diluent material, in the form of what are called unsupported catalysts (this is preferred in accordance with the invention). Examples of inert diluent materials suitable in accordance with the invention include finely divided aluminum oxide, silicon dioxide, aluminosilicates, zirconium dioxide, titanium dioxide or mixtures thereof. Undiluted unsupported catalysts are preferred in accordance with the invention.

In the case of shaped unsupported catalyst bodies, the shaping is advantageously effected with precursor powder which is not calcined until after the shaping. The shaping is effected typically with addition of shaping aids, for example graphite (lubricant) or mineral fibers (reinforcing aid). Suitable shaping processes are tableting and extrusion. It will be appreciated that the shaping may, however, also be performed, for example, with a mixture of active material powder and precursor powder, to which shaping aids and optionally inert diluent powders are again added prior to the shaping. Shaping is followed by another calcination. In principle, the shaping to unsupported catalysts can also be performed only with already prefabricated active material powder and optionally the aids mentioned. The shaping here too is generally followed by another calcination.

A favorable Mo source is, for example, ammonium heptamolybdate tetrahydrate $(NH_4)_6 (Mo_7O_{24}).4H_2O$. Advantageous iron sources are, for example, iron(III) nitrate [Fe$(NO_3)_3$], iron(III) chloride [$FeCl_3$] or hydrates of iron(III) nitrate, for example $Fe(NO_3)_3.9H_2O$.

Preferred geometries of the shaped support bodies for eggshell catalysts of the mixed oxide active materials of formula I are spheres and rings, the longest dimension of which is 1 to 10 mm, frequently 2 to 8 mm or 3 to 6 mm (the longest dimension of a shaped body in this document is generally understood to mean the longest direct line connecting two points on the surface of the shaped body).

Ring geometries favorable in accordance with the invention have hollow cylindrical shaped support bodies with a length of 2 to 10 mm, an external diameter of 4 to 10 mm and a wall thickness of 1 to 4 mm. The hollow cylindrical shaped support bodies preferably have a length of 3 to 6 mm, an external diameter of 4 to 8 mm and a wall thickness of 1 to 2 mm. In principle, the shaped support bodies may also have an irregular shape.

Suitable materials for the inert shaped support bodies are, for example, quartz, silica glass, sintered silica, sintered or fused alumina, porcelain, sintered or fused silicates such as aluminum silicate, magnesium silicate, zinc silicate, zirconium silicate, and especially steatite (e.g. C 220 steatite from CeramTec).

The inert shaped support bodies may differ from the catalytic active material normally in that they have a much lower specific surface area. In general, the specific surface area thereof is less than 3 $m^2/g$ of shaped support body. At this point, it should be emphasized that all figures in this document for specific surface areas relate to determinations according to DIN 66131 (determination of specific surface area of solids by means of gas absorption ($N_2$) according to Brunauer-Emmett-Teller (BET)).

The coating of the inert shaped support bodies with the particular finely divided powder is generally executed in a suitable rotatable vessel, for example in a coating drum. Appropriately, in some embodiments, the liquid binder is sprayed onto the inert shaped support bodies and the binder-moistened surface of the shaped support bodies being moved within the coating drum is dusted with the particular powder (see, for example, EP-A 714700). Subsequently, the adhering liquid is generally removed at least partly from the coated shaped support body (for example by passing hot gas through the coated shaped support bodies, as described in WO 2006/094765). In principle, however, it is also possible to employ all other application processes acknowledged as prior art in EP-A 714700 to produce the relevant eggshell catalysts. Useful liquid binders include, for example, water and aqueous solutions (for example of glycerol in water). For example, the coating of the shaped support bodies can also be undertaken by spraying a suspension of the pulverant material to be applied in liquid binder (for example water) onto the surface of the inert shaped support bodies (generally under the action of heat and a drying entraining gas). In principle, the coating can also be undertaken in a fluidized bed system or powder coating system.

The thickness of the eggshell of catalytically active oxide material applied to the surface of the inert shaped support body is, in the case of the mixed oxide active materials of formula I, appropriately in application terms, generally 10 to 1000 μm. The eggshell thickness is preferably 10 to 500 μm, more preferably 100 to 500 μm and most preferably 200 to 300 μm. In one embodiment, suitable ring geometries for possible inert shaped support bodies of annular eggshell oxidation catalysts A for the inventive purposes in reaction zone A are all ring geometries disclosed in DE-A 102010028328 and in DE-A 102010023312, and all disclosed in EP-A 714700.

Preferred shaped unsupported catalyst bodies comprising mixed oxide active materials I are solid cylinders, hollow cylinders and trilobes. The external diameter of cylindrical unsupported catalysts is, appropriately in application terms, 3 to 10 mm, preferably 4 to 8 mm and in particular 5 to 7 mm.

The height thereof is advantageously 1 to 10 mm, preferably 2 to 6 mm and in particular 3 to 5 mm. The same applies in the case of hollow cylinders. In addition, the internal diameter of the orifice running through from the top downward is advantageously 1 to 8 mm, preferably 2 to 6 mm and most preferably 2 to 4 mm. Appropriately in some embodiments, the wall thickness of hollow cylinders is 1 to 3 mm.

In the case of shaped unsupported catalyst bodies (unsupported catalysts), the shaping can be performed, for example, in such a way that the pulverant active material or the uncalcined precursor material thereof (the latter being preferred in accordance with the invention) is used to directly produce unsupported catalysts or unsupported catalyst precursors by compaction (for example by tableting or extrusion) to the desired catalyst geometry. The shaping optionally may be preceded by addition of assistants, for example graphite or stearic acid as lubricants, and/or shaping assistants and reinforcing assistants such as microfibers of glass, asbestos, silicon carbide or potassium titanate. In the case of annular geometries, the tableting can advantageously be undertaken as described in documents WO 2008/152079, WO 2008/087116, DE-A 102008040094, DE-A 102008040093 and WO 2010/000720. All geometries detailed in the aforementioned documents are also suitable for inventive unsupported oxidation catalysts A.

The oxidation catalysts can, however, also be employed in reaction zone A as supported catalysts. In contrast to shaped support bodies for the eggshell oxidation catalysts A, which are preferably nonporous or low in pores, in the case of supported catalysts A, the active material is introduced into the pore structure of the shaped support bodies. In this case, the starting materials are therefore comparatively porous shaped support bodies which, for example, are impregnated successively with the at least two solutions of the precursor compounds. The precipitation reaction described proceeds in the pores of the shaped support body, and the precursor compounds which form therein can subsequently be converted to the desired mixed oxide active material I by calcination. Alternatively, it is also possible to impregnate with a solution comprising all sources required in dissolved form, to dry and then to calcine (see, for example, DE-A 2442311). Otherwise, the procedure for preparation of the mixed oxide active material I oxidation catalysts may be as in the reference documents to which reference is made in this regard in this application.

These are especially documents U.S. Pat. Nos. 3,716,497, 3,846,341, EP-A 199359, DE-A 2145851, U.S. Pat. No. 3,983,073, DE-A 2533209, EP-A 2213370 and Catalysis Review, 47, pages 125-174 (2004).

It will be appreciated that, in the FORMOX process, it is not only possible to use comparatively pure methanol to obtain reaction gas input mixture A. Methanol raw materials suitable in this regard in accordance with the invention are also aqueous methanol solutions and technical-grade methanol, which can be used after appropriate evaporation to obtain reaction gas input mixture A.

It is also possible to charge reaction zone A with a fixed catalyst bed which comprises FORMOX oxidation catalysts A in a form diluted with inert shaped bodies.

The space velocity on the fixed catalyst bed present in reaction zone A of reaction gas input mixture A will, in the case of a FORMOX process employed in accordance with the invention, generally be 3500 l (STP)/l.h to 75 000 l (STP)/l.h, preferably 25 000 l (STP)/l.h to 35 000 l (STP)/l.h. The term "space velocity" is used as defined in DE-A 19927624.

Suitable reactors for execution of the FORMOX process in reaction zone A are especially also the heat exchanger reactors which have already been recommended for implementation of reaction zone A in the case of the silver process (see, for example, WO 2005/063375).

In accordance with the invention, the FORMOX process is also preferred in reaction zone A because the product gas mixture A thereof, in contrast to a product gas mixture A after the silver process, is free of molecular hydrogen.

In other words, the product gas mixture A of a heterogeneously catalyzed partial gas phase oxidation of methanol to formaldehyde after the FORMOX process is, e.g., without subjecting it to a removal process beforehand, and/or without performing a removal process thereon beforehand, the ideal formaldehyde source for formaldehyde required in reaction gas input mixture B.

Frequently, product gas mixture A is obtained in the FORMOX process at a temperature at which it can be used without further thermal pretreatment for production of reaction gas input mixture B. In many cases, the temperature of the product gas mixture A leaving reaction zone A, both in the case of the silver process and in the case of the FORMOX process, however, is different from that temperature with which it is to be used to obtain reaction gas input mixture B. Against this background, the stream of product gas mixture A, on its way from reaction zone A into reaction zone B, can flow through an indirect heat exchanger in order to match its temperature to the addition temperature envisaged for production of reaction gas input mixture B.

For the sake of completeness, it should also be added that, in the case of employment of the FORMOX process in reaction zone A, the stream Z obtained in separation zone T in the process according to the invention may serve as a suitable inert gas source for the inert gas required in reaction gas input mixture A. In some embodiments, a substream of stream Z may be recycled into reaction zone A to obtain reaction gas input mixture A.

A useful source for the acetic acid required in reaction gas input mixture B for the process according to the invention is especially the carbonylation of methanol in the liquid phase:

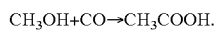
$CH_3OH+CO \rightarrow CH_3COOH$.

The reaction may be performed over a catalyst (homogeneous catalysis). Typically, the catalyst comprises at least one of the elements Fe, Co, Ni, Ru, Rh, Pd, Cu, Os, Ir and Pt, an ionic halide (e.g. KI) and/or a covalent halide (e.g. $CH_3I$) as a promoter (the iodides normally being the preferred promoters), and optionally a ligand, for example $PR_3$ or $NR_3$ where R is an organic radical. Corresponding carbonylation processes are disclosed, for example, in documents EP-A 1506151, DE 3889233 T2, EP-A 277824, EP-A 656811, DE-A 1941449, U.S. Pat. No. 6,420,304, EP-A 161874, U.S. Pat. No. 3,769,329, EP-A 55618, EP-A 87870, U.S. Pat. Nos. 5,001,259, 5,466,874 and U.S. Pat. No. 502,698, and the references cited in these documents. The working conditions require high pressures (at least 3 MPa (abs.)) and elevated temperatures (at least 150° C. or 250° C.). The catalyst system currently being employed preferentially in industrial scale processes is Rh in combination with $HI/CH_3I$ as the promoter system (see DE 68916718 T2 and U.S. Pat. No. 3,769,329). The selectivities of acetic acid formation achieved, based on methanol converted, are ≥99 mol % (Industrielle Organische Chemie, Klaus Weissermel and Hans-Jurgen Arpe, Wiley-VCH, 5th edition, 1998, page 196 and Ullmann's Encyclopedia of Industrial Chemistry, Sixth Edition, volume 6 (2003)).

Since the liquid phase carbonylation of methanol, as described above, requires the additional use of halide promoters which have strongly corrosive action and require the use of expensive corrosion-resistant construction materials, the acetic acid formed is removed by rectification from the product mixture obtained in the carbonylation of methanol for use in the process according to the invention. This is typically accomplished in a purity of acetic acid content of at least 99.8% by weight (see Industrielle Organische Chemie, Klaus Weissermel and Hans-Jurgen Arpe, Wiley-VCH, 5th edition, 1998).

By conversion of the acetic acid that is removed by rectification to the gas phase (vapor phase) and combination with product gas mixture A or product gas mixture A*, it is possible, in a comparatively simple manner, to obtain the reaction gas input mixture B required for reaction zone B.

In principle, the carbonylation of methanol to acetic acid in the liquid phase can also be performed with exclusion of halide-comprising promoters (see for example, DE-A 3606169). In this case, the acetic acid present in the crude product of the carbonylation of methanol need not necessarily be removed therefrom by rectification in order to be able to be employed for production of reaction gas input mixture B. Instead, in this case, the crude product can also be converted as such to the vapor phase and used to obtain reaction gas input mixture B.

In one embodiment, the carbonylation of methanol with carbon monoxide may be performed in the gas phase, and the resulting product gas mixture comprising the acetic acid formed will be used directly to obtain reaction gas input mixture B.

In some preferred embodiments, heterogeneously catalyzed gas phase carbonylation processes of methanol to acetic acid, which do not require presence of halogen-containing promoters, will be employed. Exemplary gas phase carbonylations of methanol to acetic acid are disclosed by U.S. Pat. No. 4,612,387 and EP-A 596632. A characteristic feature of these processes is that the catalysts employed are zeolites (aluminosilicates) with anionic structural charge, which preferably have, on their inner and/or outer surfaces, at least one cation type from the group of the cations of the elements copper, iridium, nickel, rhodium and cobalt, in order to balance out (to neutralize) the negative structural charge. Particularly advantageous zeolites are those which have a mordenite structure (see Studies in Surface, Science and Catalysis, vol. 101, 11th International Congress on Catalysis—40th Anniversary), 1996, Elsevier, Science B. V., Lausanne).

It will be appreciated that the acetic acid source (the raw material) used for reaction gas input mixture B may also be an aqueous acetic acid solution or technical-grade acetic acid solution, which can be used after appropriate evaporation to obtain reaction gas input mixture B.

Reaction gas input mixture B can be obtained by combining the stream of product gas mixture A leaving reaction zone A, or the stream of product gas mixture A* leaving separation zone T* with the acetic acid source. The acetic acid source may be converted to the vapor phase. At least one further stream may also be combined to form the reaction gas mixture B. For example, stream Y, and optionally further streams, for example additional steam or additional inert diluent gas other than steam (also referred to in this document merely as inert gas for short) may be utilized. If required, for example when product gas mixture A does not comprise any excess molecular oxygen, reaction gas input mixture B can also be produced with additional use of molecular oxygen or a mixture of inert gas and molecular oxygen, since a low (limited) oxygen content in reaction gas input mixture B generally has an advantageous effect on the service life of aldol condensation catalyst B.

The temperature of reaction gas mixture B in the process according to the invention within reaction zone B will normally be within the range from 260 to 400° C. preferably within the range from 270 to 390° C. more preferably within the range of 280 to 380° C. advantageously within the range of 300 to 370° C. and particularly advantageously within the range of 300 to 340° C.

The term "temperature of reaction gas mixture B" (also referred to in this document as reaction temperature in reaction zone B) means primarily that temperature that reaction gas mixture B has from attainment of a conversion of the formaldehyde present in reaction gas input mixture B of at least 5 mol % until attainment of the appropriate final conversion of the formaldehyde within reaction zone B. Advantageously in accordance with the invention, the temperature of reaction gas mixture B over the entire reaction zone B is within the aforementioned temperature ranges. Advantageously, reaction gas input mixture B is already supplied to reaction zone B with a temperature within the range from 260 to 400° C. Frequently, however, a charge of reaction zone B with solid inert material or of catalytically active catalyst charge highly diluted with such inert material is present at the inlet into reaction zone B in flow direction upstream of the actual catalytically active catalyst charge of reaction zone B. As it flows through such a primary charge of reaction zone B, the temperature of the reaction gas input mixture B supplied to reaction zone B can be adjusted in a comparatively simple manner to the value with which reaction gas mixture B is to enter the actual catalytically active catalyst charge of reaction zone B. In general, the temperature of the product gas mixture A leaving reaction zone A is different than this temperature.

In one embodiment, the stream of product gas mixture A, on its way from reaction zone A into reaction zone B, can flow through an indirect heat exchanger in order to approximate its temperature to the inlet temperature envisaged for reaction gas input mixture B into reaction zone B, or to bring it to this temperature.

In principle, the at least one aldol condensation catalyst B in reaction zone B can be configured in a fluidized bed. Advantageously in some embodiments, the aldol condensation catalyst B is, however, configured in a fixed bed.

With regard to the working pressure which exists in reaction zone B, the same applies correspondingly as has already been stated for the working pressure which exists in reaction zone A. In general, the working pressure in reaction zone B, due to the pressure drop which occurs as reaction gas mixture A flows through reaction zone A, is lower than the working pressure in reaction zone A. It is also possible to configure reaction zone B in corresponding heat exchanger reactors to reaction zone A, in which case the same ranges and limits apply.

The formaldehyde content in reaction gas input mixture B will, in the process according to the invention, generally be 0.5 to 10% by volume, preferably 0.5 to 7% by volume and more preferably 1 to 5% by volume.

The ratio $n_{HAc}:n_{Fd}$ of molar amount of acetic acid present in reaction gas input mixture B ($n_{HAc}$) to molar amount of formaldehyde present therein ($n_{Fd}$) in the process according to the invention is greater than 1 and may be up to 10 ($n_{Fd}$ is understood to mean the sum of formaldehyde units present in monomeric form (preferred) and possibly in oligomeric and polymeric form (formaldehyde has a tendency to such formations) in reaction gas input mixture B, since the latter undergo redissociation to monomeric formaldehyde under the reaction conditions in reaction zone B). Advantageously in accordance with the invention, the ratio $n_{HAc}:n_{Fd}$ in reaction gas input mixture B is 1.1 to 5 and more preferably 1.5 to 3.5. Frequently, the acetic acid content of reaction gas input mixture B will vary within the range from 1 or from 1.5 to 20% by volume, advantageously within the range from 2 to 15% by volume and particularly advantageously within the range from 3 to 10% by volume. The molecular oxygen content of reaction gas input mixture B varies, in the process according to the invention, appropriately in application terms, within the range from 0.5 to 5% by volume, preferably within the range from 1 to 5% by volume and more preferably within the range from 2 or from 3 to 5% by volume. Presence of molecular oxygen in reaction gas input mixture B has an advantageous effect on the service life of the catalyst charge of reaction zone B. When the oxygen content of reaction gas mixture B is too high, however, there is unwanted carbon oxide formation in reaction zone B. In principle, the molecular oxygen content in reaction gas input mixture B in the process according to the invention may, however, also be vanishingly small.

The steam content of reaction gas input mixture B in the process according to the invention should not exceed 30% by volume since the presence of steam in reaction gas mixture B has an unfavorable effect on the equilibrium position of the aldol condensation. Appropriately, in application terms, the steam content of reaction gas input mixture B will therefore generally not exceed 25% by volume and preferably not exceed 20% by volume. In general, the steam content of reaction gas input mixture B will be at least 0.5% or at least 1% by volume. Advantageously, the steam content of reaction gas input mixture B is 0.5 to 15% by volume and, taking account of the effect thereof and formation thereof in reaction zone A, in particular 1 to 10% by volume. The proportion by volume of inert diluent gases other than steam in reaction gas input mixture B will normally be at least 30% by volume. Preferably, the aforementioned inert gas content is at least 40% by volume or at least 50% by volume. In general, the proportion of inert diluent gas other than steam in reaction gas input mixture B will not exceed 95% by volume or usually 90% by volume. Particularly advantageously in application terms, reaction gas input mixture B comprises 60 to 90% by volume, particularly advantageously 70 to 80% by volume, of inert diluent gas other than steam. An inert diluent gas other than steam which is preferred in accordance with the invention is also, in reaction gas input mixture B, molecular nitrogen ($N_2$).

In some embodiments, the molecular nitrogen content of reaction gas input mixture B may be at least 30% by volume, preferably at least 40% by volume or at least 50% by volume. In one embodiment, reaction gas input mixture B comprises not more than 95% by volume and usually not more than 90% by volume of molecular nitrogen. Advantageously, reaction gas input mixture B comprises 60 to 90% by volume, particularly advantageously 70 to 80% by volume, of molecular nitrogen.

Useful catalysts for charging of reaction zone B include, for example, those disclosed in I & EC PRODUCT RESEARCH AND DEVELOPMENT, vol. 5, No. 1, March 1966, pages 50 to 53. This group of basic catalysts comprises firstly zeolites (aluminosilicates) with anionic structural charge, on the inner and outer surfaces of which at least one cation type from the group of the alkali metal ions and alkaline earth metal ions is present (preferably $Na^+$, $K^+$, $Ca^{2+}$ and/or $Mg^{2+}$)' in order to balance out (to neutralize) the negative structural charge. However, it also comprises hydroxide applied to inert supports (e.g. amorphous silicon dioxide (silica gel)), from the group consisting of alkali metal hydroxides, alkaline earth metal hydroxides and aluminum hydroxide (preferably KOH, NaOH, $Ca(OH)_2$ and $Mg(OH)_2$).

However, also suitable for charging reaction zone B are the acidic catalysts disclosed in EP-A 164614.

These are catalysts which comprise:
a) at least one oxide of at least one of the elements Si, Al, Ti, Zr, Cd, Sn, Ga, Y and La and/or zeolite, and
b) at least one oxide selected from boron oxide and phosphorus oxide, and optionally
c) one or more than one oxide of at least one of the elements V, Cr, Co, Ni, Mo and Pb and/or one or more than one heteropolyacid with at least one poly atom selected from V, Mo and W.

Preferred boron oxide is $B_2O_3$, and preferred phosphorus oxide is $P_2O_5$.

Preference is given to catalysts whose boron oxide content (calculated as $B_2O_3$ (based on the amount of B present)) is 1 to 50% by weight. In one embodiment, catalysts favorable in accordance with the invention are also those whose phosphorus oxide content (calculated as $P_2O_5$ (based on the amount of P present)) is 1 to 50% by weight. In one embodiment, useful aldol condensation catalysts B for the process according to the invention also include those among the aforementioned catalysts whose total content of phosphorus oxide (calculated as $P_2O_5$) and of boron oxide (calculated as $B_2O_3$) is 1 to 50% by weight. The aforementioned contents of phosphorus oxide and/or boron oxide are preferably 5 to 30% by weight.

In addition, constituent a) is preferably at least one oxide of at least one of the elements Si, Al, Ti and Zr.

Particularly favorable in accordance with the invention are the combinations of titanium oxide as constituent a) and boron oxide or phosphorus oxide as constituent b), or silicon dioxide-aluminum oxide as constituent a) and boron oxide as constituent b), or aluminum oxide as constituent a) and boron oxide or phosphorus oxide as constituent b). When the catalysts detailed above additionally comprise a heteropolyacid, it preferably comprises at least one of the elements P, B and Si as a heteroatom. When the aforementioned catalysts comprise a constituent c), the amount thereof is normally 0.01 to 10 mmol per gram of catalyst and in many cases 0.03 to 5 mmol per gram of catalyst. It is favorable when the catalysts have, as constituent c), both at least one of the oxides and at least one of the heteropolyacids.

More preferably in accordance with the invention, reaction zone B is, however, charged with aldol condensation catalysts B whose active material is a vanadium-phosphorus oxide and/or a vanadium-phosphorus oxide doped with elements other than vanadium and phosphorus (also referred to collectively in the literature as V—P—xO catalysts).

Such catalysts have been described before in the literature and are recommended there especially as catalysts for the heterogeneously catalyzed partial gas phase oxidation of hydrocarbons having at least four carbon atoms (especially n-butane, n-butene and/or benzene) to maleic anhydride.

Surprisingly, these catalysts known from the references for aforementioned partial oxidations are suitable in principle as aldol condensation catalysts B for charging reaction zone B.

In one embodiment, the aldol condensation catalysts B used in the process according to the invention may, for example, be selected from those disclosed in documents U.S. Pat. Nos. 5,275,996, 5,641,722, 5,137,860, 5,095,125, DE-69702728 T2, WO 2007/012620, WO 2010/072721, WO 2001/68245, U.S. Pat. No. 4,933,312, WO 2003/078310, Journal of Catalysis 107, pages 201-208 (1987), DE-A 102008040094, WO 97/12674, "Neuartige Vanadium (IV)-phosphate fur die Partialoxidation von kurzkettigen Kohlenwasserstoffen-Synthesen, Kristallstrukturen, Redox-Verhalten and katalytische Eigenschaften [Novel vanadium(IV) phosphates for the partial oxidation of short-chain hydrocarbon syntheses, crystal structures, redox behavior and catalytic properties], thesis by Ernst Benser, 2007, Rheinische Friedrichs-Wilhelms-Universitat Bonn", WO 2010/072723, "Untersuchung von V—P—O-Katalysatoren fur die partielle Oxidation von Propan zu Acrylsaure [Study of V—P—O catalysts for the partial oxidation of propane to acrylic acid], thesis by Thomas Quandt, 1999, Ruhr-Universitat Bochum", WO 2010/000720, WO 2008/152079, WO 2008/087116, DE-A 102008040093, DE-A 102005035978 and DE-A 102007005602, and the references acknowledged in these documents. In particular, this applies to all exemplary embodiments of the above prior art, especially those of WO 2007/012620.

The phosphorus/vanadium atomic ratio in the undoped or doped vanadium-phosphorus oxides is, advantageously in accordance with the invention, 0.9 to 2.0, preferably 0.9 to 1.5, more preferably 0.9 to 1.2 and most preferably 1.0 to 1.1. The arithmetic mean oxidation state of the vanadium therein is preferably +3.9 to +4.4 and more preferably 4.0 to 4.3. These active materials also advantageously have a specific BET surface area of ≥15 m²/g, preferably of ≥15 to 50 m²/g and most preferably of ≥15 to 40 m²/g. They advantageously have a total pore volume of ≥0.1 ml/g, preferably of 0.15 to 0.5 ml/g and most preferably of 0.15 to 0.4 ml/g. Total pore volume data in this document relate to determinations by the method of mercury porosimetry using the Auto Pore 9220 test instrument from Micromeritics GmbH, DE-4040 Neuss (range from 30 Angstrom to 0.3 mm). As already stated, the vanadium-phosphorus oxide active materials may be doped with promoter elements other than vanadium and phosphorus. Useful such promoter elements include the elements of groups 1 to 15 of the Periodic Table other than P and V. Doped vanadium-phosphorus oxides are disclosed, for example, by WO 97/12674, WO 95/26817, U.S. Pat. Nos. 5,137,860, 5,296,436, 5,158,923, 4,795,818 and WO 2007/012620.

Promoters preferred in accordance with the invention are the elements lithium, potassium, sodium, rubidium, cesium, thallium, molybdenum, zinc, hafnium, zirconium, titanium, chromium, manganese, nickel, copper, iron, boron, silicon, tin, niobium, cobalt and bismuth, among which preference is given not only to iron but especially to niobium, molybdenum, zinc and bismuth. The vanadium-phosphorus oxide active materials may comprise one or more promoter elements. The total content of promoters in the catalytic active material is, based on the weight thereof, generally not more than 5% by weight (the individual promoter element calculated in each case as the electrically uncharged oxide in which the promoter element has the same charge number (oxidation number) as in the active material).

Useful active materials for aldol condensation catalysts B for charging reaction zone B may be multielement oxide active materials of the general formula II

$$V_1 P_b Fe_c X^1_d X^2_e O_n \quad (II),$$

in which the variables are each defined as follows:

$X^1$ is Mo, Bi, Co, Ni, Si, Zn, Hf, Zr, Ti, Cr, Mn, Cu, B, Sn and/or Nb, preferably Nb, Mo, Zn and/or Hf, $X^2$ is Li, K, Na, Rb, Cs and/or Tl, b is 0.9 to 2.0, preferably 0.9 to 1.5, more preferably 0.9 to 1.2 and most preferably 1.0 to 1.1, c ranges from 0 to 0.1, e.g., from 0.01 to 0.5 or from 0.01 to 0.1, d ranges from 0 to 0.1, e ranges from 0 to 0.1, and n is the stoichiometric coefficient of the element oxygen, which is determined by the stoichiometric coefficients of the non-oxygen elements and the charge numbers thereof in II.

Irrespective of the stoichiometric coefficients d, e and b, the stoichiometric coefficient c is, advantageously in accordance with the invention, in active materials of the general formula II, 0.005 to 0.1, preferably 0.005 to 0.05 and particularly advantageously, 0.005 to 0.02.

The aldol condensation catalysts B may comprise the multimetal oxide active materials of the general formula II, for example, in pure, undiluted form, or diluted with an oxidic, essentially inert dilution material in the form of unsupported catalysts. Inert dilution materials suitable in accordance with the invention include, for example, finely divided aluminum oxide, silicon dioxide, aluminosilicates, zirconium dioxide, titanium dioxide or mixtures thereof. Undiluted unsupported catalysts are preferred in accordance with the invention. The unsupported catalysts may in principle be of any shape. Preferred shaped unsupported catalyst bodies are spheres, solid cylinders, hollow cylinders and trilobes, the longest dimension of which in all cases is advantageously 1 to 10 mm.

In the case of shaped unsupported catalyst bodies, the shaping may be advantageously performed with precursor powder that is calcined, e.g., after the shaping. The shaping is performed typically with addition of shaping assistants, for example graphite (lubricant) or mineral fibers (reinforcing aids). Suitable shaping processes are tableting and extrusion.

The external diameter of cylindrical unsupported catalysts is, in some embodiments, 3 to 10 mm, preferably 4 to 8 mm and in particular 5 to 7 mm. The height thereof is advantageously 1 to 10 mm, preferably 2 to 6 mm and in particular 3 to 5 mm. The same applies in the case of hollow cylinders. In addition, the internal diameter of the orifice running through from the top downward may be advantageously 1 to 8 mm, preferably 2 to 6 mm and most preferably 2 to 4 mm. A wall thickness of 1 to 3 mm may be used in the case of hollow cylinders. It will be appreciated that the doped or undoped vanadium-phosphorus oxide active materials can also be used in powder form, or as eggshell catalysts with an active material eggshell applied to the surface of inert shaped support bodies, as aldol condensation catalysts B in reaction zone B. The preparation of the eggshell catalysts, the eggshell thickness and the geometry of the inert shaped support bodies may be as is described in the case of the eggshell catalysts for reaction zone A.

In some embodiments, doped or undoped vanadium-phosphorus oxide active materials and unsupported catalysts manufactured therefrom can be produced as described in the reference documents, to which reference is made in this patent application.

For example, these documents include WO 2007/012620, WO 2010/07273, WO 2010/000720 and WO 2010/000764.

For example, the procedure may be as follows:

a) reaction of a pentavalent vanadium compound (e.g. $V_2O_5$) with an organic reducing solvent (e.g. isobutanol) in the presence of a pentavalent phosphorus compound (e.g. ortho- and/or pyrophosphoric acid) with heating to 75 to 205° C., preferably to 100 to 120° C.;

b) cooling of the reaction mixture to advantageously 40 to 90° C.;

c) optional addition of compounds comprising doping elements, for example iron(III) phosphate;

d) reheating to 75 to 205° C., preferably 100 to 120° C.;

e) isolation of the solid precursor material formed, comprising V, P, 0 and, for example, Fe (for example by filtering);

f) drying and/or thermal pretreatment of the precursor material (optionally until commencement of preforming by elimination of water from the precursor material);

g) addition of shaping aids, for example finely divided graphite or mineral fibers, and subsequent shaping to give the shaped unsupported catalyst precursor body by, for example, tableting;

h) subsequent thermal treatment of the shaped catalyst precursor bodies formed by heating in an atmosphere which comprises oxygen, nitrogen, noble gases, carbon dioxide, carbon monoxide and/or steam (for example as described in WO 2003/078310). The temperature of the thermal treatment generally exceeds 250° C., in many cases 300° C. or 350° C., but normally not 600° C., preferably not 550° C. and most preferably not 500° C.

For example, these documents include WO 2007/012620, WO 2010/07273, WO 2010/000720 and WO 2010/000764.

The space velocity of the catalyst charge on reaction zone B of formaldehyde present in reaction gas input mixture B may, in accordance with the invention, be 1 to 100, preferably 2 to 50 and more preferably 3 to 30 or 4 to 10 l(STP)/l.h. The term "space velocity" is used as defined in DE-A 19927624. Both in reaction zone A and in reaction zone B, the particular fixed catalyst bed may, in some embodiment, consist only of catalysts comprising active material, in other embodiments the bed may consist of a mixture of catalysts comprising active material and inert shaped bodies.

In some embodiments wherein V—P—O catalysts are employed as aldol condensation catalysts in reaction zone B, formaldehyde conversion, based on a single pass of reaction gas mixture B through reaction zone B, is at least 95 mol %, usually at least 98 mol %. Selectivity of acrylic acid formation, based on formaldehyde converted, is generally 95 mol %, frequently 98 mol %.

Suitable reactors for configuration of reaction zone B may be those heat exchanger reactors already discussed with respect to reaction zone A.

The product gas mixture B leaves reaction zone B and may comprise acrylic acid, unconverted acetic acid, at least one inert diluent gas other than steam, and steam, and optionally molecular oxygen. This mixture can be separated as discussed herein.

The product gas mixture B may further comprise an alkylenating agent. Preferably, the alkylenating agent is formaldehyde. For example, the product gas mixture B may comprise at least 0.05 wt % alkylenating agent(s), e.g., at least 0.1 wt. %, at least 0.5 wt %, at least 1 wt %, at least 5 wt %, at least 7 wt %, at least 10 wt %, or at least 25 wt %. In terms of ranges, the product gas mixture B may comprise from 0.05 wt % to 50 wt % alkylenating agent(s), e.g., from 0.1 wt % to 45 wt %, from 0.1 wt % to 25 wt %, from 1 wt % to 45 wt %, from 1 wt % to 25 wt %, from 1 wt % to 10 wt %, or from 5 wt % to 10 wt %. In terms of upper limits, the product gas mixture B may comprise less than 50 wt % alkylenating agent(s), e.g., less than 45 wt %, less than 25 wt %, or less than 10 wt %.

In one embodiment, the product gas mixture B further comprises water. For example, the product gas mixture B may comprise less than 60 wt % water, e.g., less than 50 wt %, less than 40 wt %, or less than 30 wt %. In terms of ranges, the product gas mixture B may comprise from 1 wt % to 60 wt % water, e.g., from 5 wt % to 50 wt %, from 10 wt % to 40 wt %, or from 15 wt % to 40 wt %. In terms of upper limits, the product gas mixture B may comprise at least 1 wt % water, e.g., at least 5 wt %, at least 10 wt %, or at least 15 wt %.

In one embodiment, the product gas mixture B of the present invention comprises very little, if any, of the impurities found in most conventional acrylic acid crude product streams. For example, the product gas mixture B of the present invention may comprise less than 1000 wppm of such impurities (either as individual components or collectively), e.g., less than 500 wppm, less than 100 wppm, less than 50 wppm, or less than 10 wppm. Exemplary impurities include acetylene, ketene, beta-propiolactone, higher alcohols, e.g., $C_{2+}$, $C_{3+}$, or $C_{4+}$, and combinations thereof. Importantly, the product gas mixture B of the present invention comprises very little, if any, furfural and/or acrolein. In one embodiment, the product gas mixture B comprises substantially no furfural and/or acrolein, e.g., no furfural and/or acrolein. In one embodiment, the product gas mixture B comprises less than less than 500 wppm acrolein, e.g., less than 100 wppm, less than 50 wppm, or less than 10 wppm. In one embodiment, the product gas mixture B comprises less than less than 500 wppm furfural, e.g., less than 100 wppm, less than 50 wppm, or less than 10 wppm. Furfural and acrolein are known to act as detrimental chain terminators in acrylic acid polymerization reactions. Also, furfural and/or acrolein are known to have adverse effects on the color of purified product and/or to subsequent polymerized products.

In addition to the acrylic acid and the alkylenating agent, the product gas mixture B may further comprise acetic acid, water, propionic acid, and light ends such as oxygen, nitrogen, carbon monoxide, carbon dioxide, methanol, methyl acetate, methyl acrylate, acetaldehyde, hydrogen, and acetone. Exemplary compositional data for the product gas mixture B are shown in Table 1. Components other than those listed in Table 1 may also be present in the product gas mixture B.

TABLE 1

PRODUCT GAS MIXTURE COMPOSITIONS

| Component | Conc. (wt %) | Conc. (wt %) | Conc. (wt %) | Conc. (wt %) |
|---|---|---|---|---|
| Acrylic Acid | 1 to 75 | 1 to 50 | 5 to 50 | 10 to 40 |
| Alkylenating Agent(s) | 0.05 to 50 | 1 to 45 | 1 to 25 | 1 to 10 |
| Acetic Acid | 1 to 90 | 1 to 70 | 5 to 50 | 10 to 50 |
| Water | 1 to 60 | 5 to 50 | 10 to 40 | 15 to 40 |
| Propionic Acid | 0.01 to 10 | 0.1 to 10 | 0.1 to 5 | 0.1 to 1 |
| Oxygen | 0.01 to 10 | 0.1 to 10 | 0.1 to 5 | 0.1 to 1 |
| Nitrogen | 0.1 to 20 | 0.1 to 10 | 0.5 to 5 | 0.5 to 4 |
| Carbon Monoxide | 0.01 to 10 | 0.1 to 10 | 0.1 to 5 | 0.5 to 3 |
| Carbon Dioxide | 0.01 to 10 | 0.1 to 10 | 0.1 to 5 | 0.5 to 3 |
| Other Light Ends | 0.01 to 10 | 0.1 to 10 | 0.1 to 5 | 0.5 to 3 |

In one embodiment, deactivation of the different catalysts in the different reaction zones of the process according to the invention can be counteracted by correspondingly increasing the reaction temperature in the particular reaction zone (in order to keep the reactant conversion based on a single pass of the reaction gas mixture through the catalyst charge stable). It is also possible to regenerate the oxidic active materials of reaction zones A and B in a manner corresponding to that described for comparable oxidic catalysts in WO 2005/042459, by passing over an oxidizing oxygen-comprising gas at elevated temperature.

Reliable operation, especially in reaction zone A, can be ensured in the process according to the invention by an analogous application of the procedure described in WO 2004/007405.

The process according to the invention is advantageous for its broad and wide-ranging raw material basis in terms of time. In addition, the process, in contrast to the prior art processes, enables a smooth transition from "fossil acrylic acid" to "renewable acrylic acid" while maintaining the procedure.

"Fossil acrylic acid" is understood to mean acrylic acid for which the ratio of the molar amount of $^{14}C$ atomic nuclei present in this acrylic acid to the molar amount of $^{12}C$ atomic nuclei present in the same acrylic acid, $n^{14}C:n^{12}C$, is small.

"Renewable acrylic acid" is understood to mean acrylic acid for which the $n^{14}C:n^{12}C$ ratio corresponds to V*, the ratio of $n^{14}C:n^{12}C$ present in the $CO_2$ in the earth's atmosphere, the $n^{14}C:n^{12}C$ ratio being determined by the procedure developed by Willard Frank Libby (http://de.wikipedia.orgn/wiki/Radikohlenstoffdatierung).

The terms "renewable carbon" and "fossil carbon" are used correspondingly in this document.

The process developed by Libby is based on the fact that, compared to the two carbon atom nuclei $^{12}C$ and $^{13}C$, the third naturally occurring carbon nucleus $^{14}C$ is unstable and is therefore also referred to as radiocarbon having a half-life of approximately 5700 years.

In the upper layers of the earth's atmosphere, $^{14}C$ is constantly being newly formed by nuclei reaction. At the same time, $^{14}C$ decomposes with a half-life of 5700 years by β-decomposition. An equilibrium forms in the earth's atmosphere between constant new formation and constant degradation, and so the proportion of the $^{14}C$ nuclei in the carbon in the atmosphere on earth is constant over long periods; a stable ratio V* is present in the earth's atmosphere.

The radiocarbon produced in the atmosphere combines with atmospheric oxygen to give $CO_2$, which then gets into the biosphere as a result of photosynthesis. Since life forms (plants, animals, humans), in the course of their metabolism, constantly exchange carbon with the atmosphere surrounding them in this way, the same distribution ratio of the three carbon isotopes and hence the same $n^{14}C:n^{12}C$ ratio is established in living organisms as is present in the surrounding atmosphere.

When this exchange is stopped at the time of death of the life form, the ratio between $^{14}C$ and $^{12}C$ in the dead organism changes because the decomposing $^{14}C$ atomic nucleic are no longer replaced by new ones (the carbon present in the dead organism becomes fossil).

If the death of the organism (life form) was more than 50 000 years ago, the $^{14}C$ content thereof is below the detection limit. Present and future biological ("renewable") raw materials and chemicals produced therefrom have the particular current $^{14}C$ concentration in the $CO_2$ in the atmosphere on the earth (this $n^{14}C:n^{12}C$ ratio is represented by V*). Fossil carbon sources such as coal, mineral oil or natural gas, however, have already lain "dead" in the earth for several million years, just like chemicals produced therefrom, no longer comprise any $^{14}C$.

When fossil acetic acid (acetic acid obtained from fossil raw materials) and renewable formaldehyde (formaldehyde obtained from methanol obtained from renewable raw materials) are used in the process according to the invention, an acrylic acid is obtained whose $n^{14}C:n^{12}C$ ratio is only approximately (⅓)×V.

When, in the process according to the invention, in contrast, acetic acid obtained from renewable raw materials and formaldehyde obtained from fossil methanol are used, an acrylic acid is obtained whose $n^{14}C:n^{12}C$ ratio is approximately (⅔)×V.

When, in the process according to the invention, both fossil (renewable) acetic acid and fossil (renewable) formaldehyde are used, an acrylic acid is obtained whose $n^{14}C:n^{12}C$ ratio is essentially zero.

When the possibility of blending renewable and fossil starting materials (raw materials) is additionally considered in the process according to the invention, the manufacturer of acrylic acid, when employing the inventive procedure, is able to adjust the "renewable level" of the acrylic acid to be supplied to this customer (the $n^{14}C:n^{12}C$ ratio desired by the customer for the acrylic acid to be supplied) without altering the preparation process, e.g., with one and the same production plant.

By esterifying an acrylic acid for which V=V* with biomethanol or bioethanol, it is possible to obtain acrylic esters whose $n^{14}C$ to $n^{12}C$ ratio is likewise V*.

A further advantage of the inventive procedure is that the target product of reaction zone A does not require removal from product gas mixture A in order to be able to be employed for production of reaction gas input mixture B. This ensures both high economy and an efficient energy balance for the process according to the invention. Furthermore, in the case of condensation of acetic acid with formaldehyde, neither glyoxal nor propionic acid is formed as a by-product, as is necessarily the case for a heterogeneously catalyzed partial oxidation of propylene, propane, acrolein, propionaldehyde and/or glycerol to acrylic acid (see WO 2010/074177).

Furthermore, the process according to the invention ensures a high space-time yield coupled with simultaneously high target product selectivity based on the reactants converted.

Separation

In additional embodiments, the unique crude acrylate stream of the present invention may be separated in a separation zone to form a final product, e.g., a final acrylic acid product. It is contemplated that any of the various components and/or features discussed herein or shown in the FIGS.

may be used in conjunction with one or more other components and/or features discuss herein or shown in the FIGS. FIG. 1 is a flow diagram depicting the formation of the crude acrylate stream and the separation thereof to obtain acrylate product 118. Acrylate product system 100 comprises oxidation reaction zone 101, condensation reaction zone 102 and separation zone 104. Oxidation reaction zone comprises oxidation reactor 103, oxidation reaction gas mixture A feed 105, oxidation product gas mixture A outlet 107 and acetic acid feed 109. Condensation reaction zone 102 comprises reactor 106, condensation reaction gas mixture B feed, e.g., acetic acid and formaldehyde feed 110, and vaporizer 112.

An oxidation reaction gas mixture is fed to oxidation reactor 103 via oxidation reaction gas mixture A feed 105. The oxidation reaction gas mixture A may comprise methanol and oxygen. The oxidation reaction gas may optionally further comprise steam and/or at least one diluent other than steam. The reactants in the reaction gas mixture are reacted under conditions effective to form an oxidation product gas mixture that exits via oxidation product gas mixture A 107. The product gas mixture may comprise formaldehyde, steam, and at least one inert diluent other than steam. The reaction may be conducted over at least one of the oxidation catalysts discussed herein.

Acetic acid is fed to oxidation reaction zone 101 via acetic acid feed 109. The contents of acetic acid feed 109 contact, e.g., are combined with, at least a portion of the product gas mixture A in oxidation product gas mixture A outlet 107 to form condensation reaction gas mixture B, which is conveyed to the condensation reaction zone via line 110. The condensation reaction gas mixture B comprises acetic acid, formaldehyde, steam and at least one diluent gas other than steam.

The condensation reaction gas mixture A (or at least a portion thereof) is directed to vaporizer 112 via line 110. The gas mixture need not be in gas form. In some embodiments, the reaction mixture may be in liquid form. In some embodiments the alkanoic acid, e.g., acetic acid, either as a fresh feed or a recycled feed, may be in liquid form. The vaporizer vaporizes the condensation reactants and yields a vapor feed stream, which exits vaporizer 112 via line 114 and is directed to reactor 106. In one embodiment, the acetic acid in line 109 may be fed separately to vaporizer 112 and the reactants may be combined with one another in vaporizer 112. In one embodiment, the condensation product gas mixture A and the acetic acid are fed directly to condensation reactor 106 where they are combined with one another (not shown). The temperature of the vapor feed stream in line 114 is preferably from 200° C. to 600° C., e.g., from 250° C. to 500° C. or from 340° C. to 425° C. In one embodiment, a vaporizer may not be employed and the reactants may be fed directly to reactor 106.

Any feed that is not vaporized may be removed from vaporizer 112 and may be recycled or discarded. In addition, although line 114 is shown as being directed to the upper half of reactor 106, line 114 may be directed to the middle or bottom of reactor 106. Further modifications and additional components to reaction zone 102 and separation zone 104 are described below.

At least a portion of the acetic acid in the condensation reaction gas mixture B is reacted with with at least a portion of the formaldehyde in condensation reaction gas mixture B under conditions effective to form a condensation product gas mixture B, which exits the reactor via line 116. The condensation product gas mixture B comprises acrylic acid, acetic acid, steam, and at least one inert diluent gas other than steam.

Reactor 106 contains at least one aldol condensation catalyst that is used in the reaction to form the condensation product gas mixture B, which is withdrawn, preferably continuously, from reactor 106 via line 116. The aldol condensation catalyst may be as discussed herein. Although FIG. 1 shows the condensation product gas mixture B being withdrawn from the bottom of reactor 106, the condensation product gas mixture B may be withdrawn from any portion of reactor 106.

Exemplary composition ranges for the condensation product gas mixture B are shown in Table 1.

In one embodiment, one or more guard beds (not shown) may be used upstream of the one or more of the reactors to protect the catalyst from poisons or undesirable impurities contained in the feed or return/purge streams. Such guard beds may be employed in the vapor or liquid acrylate streams. Suitable guard bed materials may include, for example, carbon, silica, alumina, ceramic, or resins. In one aspect, the guard bed media is functionalized, e.g., silver functionalized, to trap particular species such as sulfur or halogens.

Condensation product gas mixture B in line 116 is fed to separation zone 104. Separation zone 104 may comprise one or more separation units, e.g., two or more or three or more. Separation zone 104 separates the condensation product gas mixture B to yield a finished acrylate product, which exits via line 118.

Figure 2:
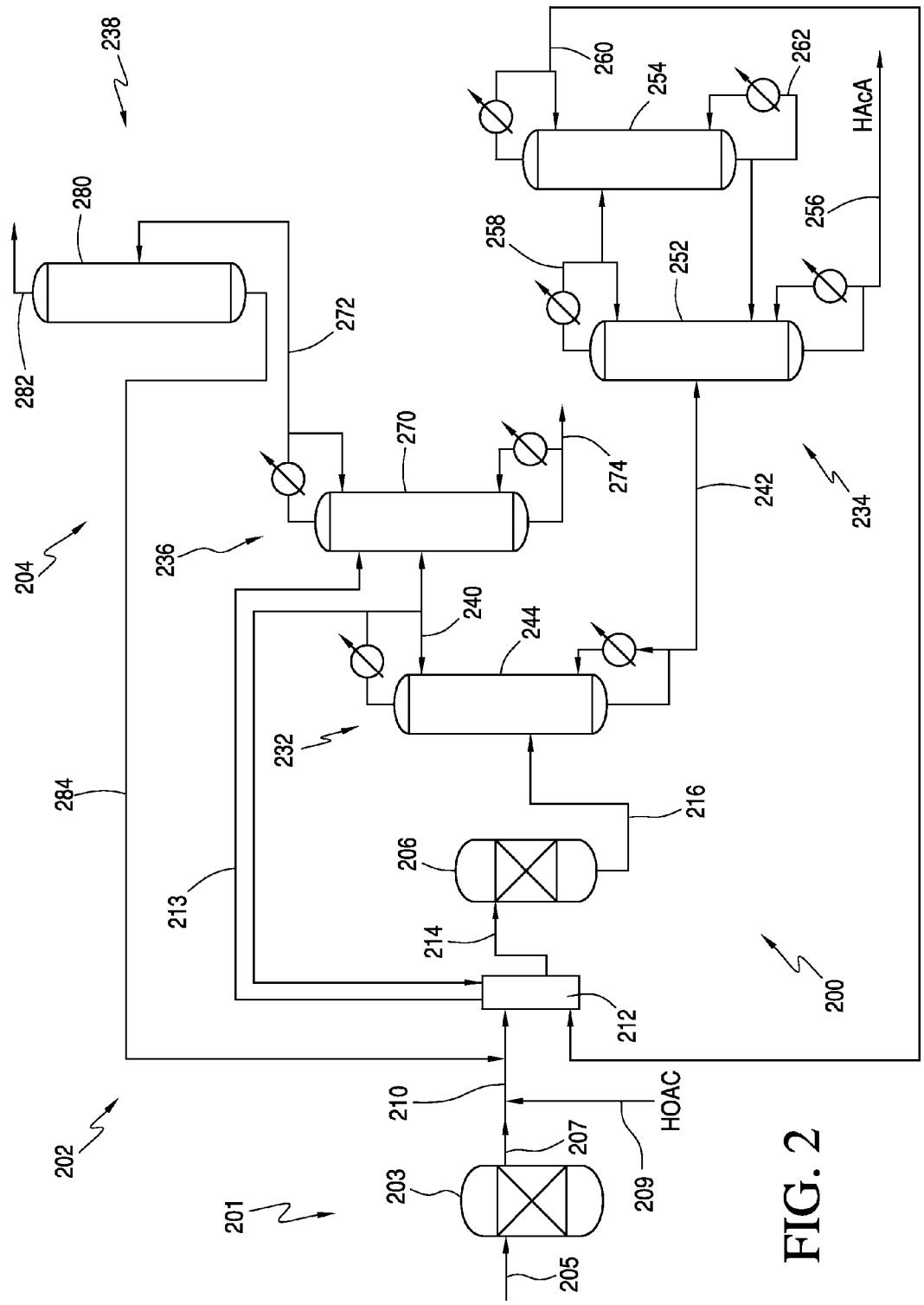
FIG. 2 is a schematic of an acrylic acid reaction/separation system in accordance with an embodiment of the present invention.

FIG. 2 shows an overview of a reaction/separation scheme in accordance with the present invention. Acrylate product system 200 comprises oxidation reaction zone 201, condensation reaction zone 202 and separation zone 204. Oxidation reaction zone comprises oxidation reactor 203, oxidation reaction gas mixture A feed 205, oxidation product gas mixture A outlet 207 and acetic acid feed 209. Condensation reaction zone 202 comprises reactor 206, condensation reaction gas mixture B feed, e.g., acetic acid and formaldehyde feed 210, and vaporizer 212. Reaction zone 202 and the components thereof function in a manner similar to reaction zone 102 of FIG. 1.

Condensation reaction zone 202 yields a condensation product gas mixture B, which exits reaction zone 202 via line 216 and is directed to separation zone 204. The components of the condensation product gas mixture B are discussed above.

As shown in FIG. 2, separation zone 204 contains multiple columns. Separation zone 204 comprises alkylenating agent split unit 232, acrylate product split unit 234, drying unit 236, and methanol removal unit 238. In one embodiment, the inventive process comprises the step of separating at least a portion of the condensation product gas mixture B to form an alkylenating agent stream and an intermediate product stream. This separating step may be referred to as the "akylenating agent split."

Exemplary compositional ranges for the intermediate acrylate product stream are shown in Table 2. Components other than those listed in Table 2 may also be present in the intermediate acrylate product stream. Examples include methanol, methyl acetate, methyl acrylate, dimethyl ketone, carbon dioxide, carbon monoxide, oxygen, nitrogen, and acetone.

TABLE 2

INTERMEDIATE ACRYLATE PRODUCT STREAM COMPOSITION

|  | Conc. (wt. %) | Conc. (wt. %) | Conc. (wt. %) |
|---|---|---|---|
| Acrylic Acid | at least 5 | 5 to 99 | 35 to 65 |
| Acetic Acid | less than 95 | 5 to 90 | 20 to 60 |
| Water | less than 50 | 0.1 to 30 | 0.5 to 20 |
| Alkylenating Agent | <1 | <0.5 | <0.1 |
| Propionic Acid | <10 | 0.01 to 5 | 0.01 o 1 |

In one embodiment, the alkylenating agent stream comprises significant amounts of alkylenating agent(s). For example, the alkylenating agent stream may comprise at least 0.01 wt. % alkylenating agent(s), e.g., at least 0.1 wt %, at least 0.5 wt %, at least 1 wt %, at least 5 wt. %, at least 10 wt. %, at least 15 wt. %, or at least 25 wt. %. In terms of ranges, the alkylenating agent stream may comprise from 0.01 wt. % to 75 wt. % alkylenating agent(s), e.g., from 0.5 wt % to 75 wt %, from 1 wt % to 50 wt %, from 3 to 50 wt. %, from 3 wt. % to 25 wt. %, or from 10 wt. % to 20 wt. %. In terms of upper limits, the alkylenating stream may comprise less than 75 wt. % alkylenating agent(s), e.g. less than 50 wt. % or less than 40 wt. %. In preferred embodiments, the alkylenating agent is formaldehyde.

It has been found that the presence of alkylenating agent, e.g., formaldehyde, (even in small amounts) in condensation product gas mixture B adds unpredictability and problems to separation schemes. Without being bound by theory, it is believed that formaldehyde reacts in many side reactions with water to form by-products. The following side reactions are exemplary.

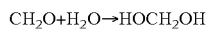

$CH_2O+H_2O \rightarrow HOCH_2OH$

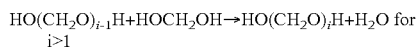

$HO(CH_2O)_{i-1}H+HOCH_2OH \rightarrow HO(CH_2O)_iH+H_2O$ for $i>1$

Without being bound by theory, it is believed that, in some embodiments, as a result of these reactions, the alkylenating agent, e.g., formaldehyde, acts as a "light" component at higher temperatures and as a "heavy" component at lower temperatures. The reaction(s) are exothermic. Accordingly, the equilibrium constant increases as temperature decreases and decreases as temperature increases. At lower temperatures, the larger equilibrium constant favors methylene glycol and oligomer production and formaldehyde becomes limited, and, as such, behaves as a heavy component. At higher temperatures, the smaller equilibrium constant favors formaldehyde production and methylene glycol becomes limited. As such, formaldehyde behaves as a light component. In view of these difficulties, as well as others, the separation of streams that comprise water and formaldehyde cannot be expected to behave as a typical two-component system. These features contribute to the unpredictability and difficulty of the separation of the unique condensation product gas mixture B of the present invention.

The present invention, surprisingly and unexpectedly, achieves effective separation of alkylenating agent(s) from the inventive condensation product gas mixture B to yield a purified product comprising acrylate product and very low amounts of other impurities. It has now been discovered that by first removing a good portion of the alkylenating agent from condensation product gas mixture B, the efficiency of the remaining separations are made more efficient. Without being bound by theory, it is believed that the removal of alkylenating agent early in the separation process lessens the separation burden on the remaining separation units. Without removing the alkylenating agent, e.g., formaldehyde, in accordance with the present invention, each additional separation unit would be burdened with separation of residual formaldehyde, which is known to be difficult. The separation schemes of some of the references, in contrast to the embodiments of the present invention, focus on separation of acrylic acid, acetic acid, and inert diluent. The difficult separation of alkylenating agent, e.g., formaldehyde, is not discussed in detail.

In one embodiment, the alkylenating split is performed such that a lower amount of acetic acid is present in the resulting alkylenating stream. Preferably, the alkylenating agent stream comprises little or no acetic acid. As an example, the alkylenating agent stream, in some embodiments, comprises less than 50 wt. % acetic acid, e.g., less than 45 wt. %, less than 25 wt. %, less than 10 wt. %, less than 5 wt. %, less than 3 wt. %, or less than 1 wt. %. Surprisingly and unexpectedly, the present invention provides for the lower amounts of acetic acid in the alkylenating agent stream, which, beneficially reduces or eliminates the need for further treatment of the alkylenating agent stream to remove acetic acid. In some embodiments, the alkylenating agent stream may be treated to remove water therefrom, e.g., to purge water.

In some embodiments, the alkylenating agent split is performed in at least one column, e.g., at least two columns or at least three columns. Preferably, the alkylenating agent is performed in a two column system. In other embodiments, the alkylenating agent split is performed via contact with an extraction agent. In other embodiments, the alkylenating agent split is performed via precipitation methods, e.g., crystallization, and/or azeotropic distillation. Of course, other suitable separation methods may be employed either alone or in combination with the methods mentioned herein.

Without being bound by theory, it is believed that alkylenating agents, e.g., formaldehyde, may not be sufficiently volatile at lower pressures. Thus, maintenance of the separation unit pressures, e.g., column pressures, at low levels surprisingly and unexpectedly provides for efficient separation operations. In addition, it has surprisingly and unexpectedly been found that maintenance of these low pressures may inhibit and/or eliminate polymerization of the acrylate products, e.g., acrylic acid, which may contribute to fouling of the column(s). Also, it has surprisingly and unexpectedly been found that by maintaining the temperature of the units, e.g., columns, at a low level (as discussed below), may inhibit and/or eliminate polymerization of the acrylate products.

The intermediate product stream comprises acrylate products. In one embodiment, the intermediate product stream comprises a significant portion of acrylate products, e.g., acrylic acid. For example, the intermediate product stream may comprise at least 5 wt. % acrylate products, e.g., at least 25 wt. %, at least 40 wt. %, at least 50 wt. %, or at least 60 wt. %. In terms of ranges, the intermediate product stream may comprise from 5 wt. % to 99 wt. % acrylate products, e.g. from 10 wt. % to 90 wt. %, from 25 wt. % to 75 wt. %, or from 35 wt. % to 65 wt. %. The intermediate product stream, in one embodiment, comprises little if any alkylenating agent. For example, the intermediate product stream may comprise less than 1 wt. % alkylenating agent, e.g., less than 0.1 wt. % alkylenating agent, less than 0.05 wt. %, or less than 0.01 wt. %. In addition to the acrylate products, the intermediate product stream optionally comprises acetic acid, water, propionic acid and other components.

In some cases, the intermediate acrylate product stream comprises higher amounts of alkylenating agent. For example, in one embodiment, the intermediate acrylate product stream comprises from 1 wt. % to 50 wt. % alkylenating agent, e.g., from 1 wt. % to 10 wt. % or from 5 wt. % to 50 wt. %. In terms of limits, the intermediate acrylate product stream may comprise at least 1 wt. % alkylenating agent, e.g., at least 5 wt. % or at least 10 wt. %.

In one embodiment, condensation product gas mixture B is optionally treated, e.g. separated, prior to the separation of alkylenating agent therefrom. In such cases, the treatment(s) occur before the alkylenating agent split is performed. In other embodiments, at least a portion of the intermediate acrylate product stream may be further treated after the alkylenating agent split. As one example, condensation product gas mixture B may be treated to remove light ends therefrom. This treatment may occur either before or after the alkylenating agent split, preferably before the alkylenating agent split. In some of these cases, the further treatment of the intermediate acrylate product stream may result in derivative streams that may be considered to be additional purified acrylate product streams. In other embodiments, the further treatment of the intermediate acrylate product stream results in at least one finished acrylate product stream.

In one embodiment, the inventive process operates at a high process efficiency. For example, the process efficiency may be at least 10%, e.g., at least 20% or at least 35%. In one embodiment, the process efficiency is calculated based on the flows of reactants into the reaction zone. The process efficiency may be calculated by the following formula.

Process Efficiency=$2N_{HAcA}/[N_{HOAc}+N_{Trioxane}+N_{water}]$ where:

$N_{HAcA}$ is the molar production rate of acrylate products; and $N_{HOAc}$, $N_{HCHO}$, and $N_{water}$ are the molar feed rates of acetic acid, alkylenating agent, and water, if any.

In other embodiments, the intermediate acrylate product stream comprises higher amounts of alkylenating agent. For example, the intermediate acrylate product stream may comprise from 1 wt. % to 10 wt. % alkylenating agent, e.g., from 1 wt. % to 8 wt. % or from 2 wt. % to 5 wt. %. In one embodiment, the intermediate acrylate product stream comprises greater than 1 wt. % alkylenating agent, e.g., greater than 5 wt. % or greater than 10 wt. %.

Exemplary compositional ranges for the alkylenating agent stream are shown in Table 3. Components other than those listed in Table 3 may also be present in the purified alkylate product stream. Examples include methanol, methyl acetate, methyl acrylate, dimethyl ketone, carbon dioxide, carbon monoxide, oxygen, nitrogen, and acetone.

TABLE 3

ALKYLENATING AGENT STREAM COMPOSITION

| | Conc. (wt. %) | Conc. (wt. %) | Conc. (wt. %) |
|---|---|---|---|
| Acrylic Acid | less than 15 | 0.01 to 10 | 0.1 to 5 |
| Acetic Acid | 10 to 65 | 20 to 65 | 25 to 55 |
| Water | 15 to 75 | 25 to 65 | 30 to 60 |
| Alkylenating Agent | at least 0.01 | 0.01 to 75 | 0.1 to 20 |
| Propionic Acid | <10 | 0.01 5 | 0.02 1 |

In other embodiments, the alkylenating stream comprises lower amounts of acetic acid. For example, the alkylenating agent stream may comprise less than 10 wt. % acetic acid, e.g., less than 5 wt. % or less than 1 wt. %.

As mentioned above, condensation product gas mixture B of the present invention comprises little, if any, furfural and/or acrolein. As such the derivative stream(s) of condensation product gas mixture B will comprise little, if any, furfural and/or acrolein. In one embodiment, the derivative stream(s), e.g., the streams of the separation zone, comprises less than less than 500 wppm acrolein, e.g., less than 100 wppm, less than 50 wppm, or less than 10 wppm. In one embodiment, the derivative stream(s) comprises less than less than 500 wppm furfural, e.g., less than 100 wppm, less than 50 wppm, or less than 10 wppm.

Separation zone 204 may also comprise a light ends removal unit (not shown). For example, the light ends removal unit may comprise a condenser and/or a flasher. The light ends removal unit may be configured either upstream of the alkylenating agent split unit. Depending on the configuration, the light ends removal unit removes light ends from the crude acrylate stream, the alkylenating stream, and/or the intermediate acrylate product stream. In one embodiment, when the light ends are removed, the remaining liquid phase comprises the acrylic acid, acetic acid, alkylenating agent, and/or water.

Alkylenating agent split unit 232 may comprise any suitable separation device or combination of separation devices. For example, alkylenating agent split unit 232 may comprise a column, e.g., a standard distillation column, an extractive distillation column and/or an azeotropic distillation column. In other embodiments, alkylenating agent split unit 232 comprises a precipitation unit, e.g., a crystallizer and/or a chiller. Preferably, alkylenating agent split unit 232 comprises a single distillation column.

In another embodiment, the alkylenating agent split is performed by contacting condensation product gas mixture B with a solvent that is immiscible with water. For example, alkylenating agent split unit 232 may comprise at least one liquid-liquid extraction column. In another embodiment, the alkylenating agent split is performed via azeotropic distillation, which employs an azeotropic agent. In these cases, the azeotropic agent may be selected from the group consisting of methyl isobutylketene, o-xylene, toluene, benzene, n-hexane, cyclohexane, p-xylene, and mixtures thereof. This listing is not exclusive and is not meant to limit the scope of the invention. In another embodiment, the alkylenating agent split is performed via a combination of distillations, e.g., standard distillation, and crystallization. Of course, other suitable separation devices may be employed either alone or in combination with the devices mentioned herein.

In FIG. 2, alkylenating agent split unit 232 comprises first column 244. The condensation product gas mixture in line 216 is directed to first column 244. First column 244 separates condensation product gas mixture B to form a distillate in line 240 and a residue in line 242. The distillate may be refluxed and the residue may be boiled up as shown. Stream 240 comprises at least 1 wt % alkylenating agent. As such, stream 240 may be considered an alkylenating agent stream. The first column residue exits first column 244 in line 242 and comprises a significant portion of acrylate product. As such, stream 242 is an intermediate product stream. In one embodiment, at least a portion of stream 240 is directed to drying unit 236.

Exemplary compositional ranges for the distillate and residue of first column 244 are shown in Table 4. Components other than those listed in Table 4 may also be present in the residue and distillate.

TABLE 4

FIRST COLUMN

| | Conc. (wt. %) | Conc. (wt. %) | Conc. (wt. %) |
|---|---|---|---|
| Distillate | | | |
| Acrylic Acid | less than 5 | less than 3 | 0.05 to 1 |
| Acetic Acid | less than 10 | less than 5 | 0.5 to 3 |
| Water | 40 to 90 | 45 to 85 | 50 to 80 |
| Alkylenating Agent | at least 0.1 | 1 to 75 | 10 to 40 |
| Propionic Acid | less than 10 | less than 5 | less than 1 |
| Methanol | less than 5 | less than 1 | less than 0.5 |
| Residue | | | |
| Acrylic Acid | 10 to 80 | 15 to 65 | 20 to 50 |
| Acetic Acid | 40 to 80 | 45 to 70 | 50 to 65 |
| Water | 1 to 40 | 1 to 20 | 1 to 10 |

TABLE 4-continued

| FIRST COLUMN | | | |
|---|---|---|---|
| | Conc. (wt. %) | Conc. (wt. %) | Conc. (wt. %) |
| Alkylenating Agent | at least 0.001 | 0.001 to 50 | 0.001 to 10 |
| Propionic Acid | less than 10 | less than 5 | less than 1 |

In one embodiment, the first distillate comprises smaller amounts of acetic acid, e.g., less than 25 wt %, less than 10 wt %, e.g., less than 5 wt % or less than 1 wt %. In one embodiment, the first residue comprises larger amounts of alkylenating agent.

In some embodiments, the intermediate acrylate product stream comprises higher amounts of alkylenating agent, e.g., greater than 1 wt % greater than 5 wt % or greater than 10 wt %.

For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

In one embodiment, polymerization inhibitors and/or anti-foam agents may be employed in the separation zone, e.g., in the units of the separation zone. The inhibitors may be used to reduce the potential for fouling caused by polymerization of acrylates. The anti-foam agents may be used to reduce potential for foaming in the various streams of the separation zone. The polymerization inhibitors and/or the anti-foam agents may be used at one or more locations in the separation zone.

In cases where any of alkylenating agent split unit 232 comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 100 kPa, less than 80 kPa, or less than 60 kPa. In terms of lower limits, the column(s) may be operated at a pressures of at least 1 kPa, e.g., at least 20 kPa or at least 40 kPa. The surprising and unexpected benefits of these temperatures and pressure ranges and limits are discussed herein.

In one embodiment, the alkylenating agent split is achieved via one or more liquid-liquid extraction units. Preferably, the one or more liquid-liquid extraction units employ one or more extraction agents. Multiple liquid-liquid extraction units may be employed to achieve the alkylenating agent split. Any suitable liquid-liquid extraction devices used for multiple equilibrium stage separations may be used. Also, other separation devices, e.g., traditional columns, may be employed in conjunction with the liquid-liquid extraction unit(s).

In one embodiment (not shown), condensation product gas mixture B is fed to a liquid-liquid extraction column where condensation product gas mixture B is contacted with an extraction agent, e.g., an organic solvent. The liquid-liquid extraction column extracts the acids, e.g., acrylic acid and acetic acid, from condensation product gas mixture B. An aqueous phase comprising water, alkylenating agent, and some acetic acid exits the liquid-liquid extraction unit. Small amounts of acrylic acid may also be present in the aqueous stream. The aqueous phase may be further treated and/or recycled. An organic phase comprising acrylic acid, acetic acid, and the extraction agent also exits the liquid-liquid extraction unit. The organic phase may also comprise water and formaldehyde. The acrylic acid may be separated from the organic phase and collected as product. The acetic acid may be separated then recycled and/or used elsewhere. The solvent may be recovered and recycled to the liquid-liquid extraction unit.

The inventive process further comprises the step of separating the intermediate acrylate product stream to form a finished acrylate product stream and a first finished acetic acid stream. The finished acrylate product stream comprises acrylate product(s) and the first finished acetic acid stream comprises acetic acid. The separation of the acrylate products from the intermediate product stream to form the finished acrylate product may be referred to as the "acrylate product split."

Returning to FIG. 2, intermediate product stream 242 exits alkylenating agent split unit 232 and is directed to acrylate product split unit 234 for further separation, e.g., to further separate the acrylate products therefrom. Acrylate product split unit 234 may comprise any suitable separation device or combination of separation devices. For example, acrylate product split unit 234 may comprise at least one column, e.g., a standard distillation column, an extractive distillation column and/or an azeotropic distillation column. In other embodiments, acrylate product split unit 234 comprises a precipitation unit, e.g., a crystallizer and/or a chiller. Preferably, acrylate product split unit 234 comprises two standard distillation columns as shown in FIG. 2. In another embodiment, acrylate product split unit 234 comprises a liquid-liquid extraction unit. Of course, other suitable separation devices may be employed either alone or in combination with the devices mentioned herein.

In FIG. 2, acrylate product split unit 234 comprises second column 252 and third column 254. Acrylate product split unit 234 receives at least a portion of purified acrylic product stream in line 242 and separates same into finished acrylate product stream 256 and at least one acetic acid-containing stream. As such, acrylate product split unit 234 may yield the finished acrylate product.

As shown in FIG. 2, at least a portion of purified acrylic product stream in line 242 is directed to second column 252. Second column 252 separates the purified acrylic product stream to form second distillate, e.g., line 258, and second residue, which is the finished acrylate product stream, e.g., line 256. The distillate may be refluxed and the residue may be boiled up as shown.

Stream 258 comprises acetic acid and some acrylic acid. The second column residue exits second column 252 in line 256 and comprises a significant portion of acrylate product. As such, stream 256 is a finished product stream. Exemplary compositional ranges for the distillate and residue of second column 252 are shown in Table 5. Components other than those listed in Table 5 may also be present in the residue and distillate.

TABLE 5

| SECOND COLUMN | | | |
|---|---|---|---|
| | Conc. (wt. %) | Conc. (wt. %) | Conc. (wt. %) |
| Distillate | | | |
| Acrylic Acid | 0.1 to 40 | 1 to 30 | 5 to 30 |
| Acetic Acid | 60 to 99 | 70 to 90 | 75 to 85 |
| Water | 0.1 to 25 | 0.1 to 10 | 1 to 5 |

TABLE 5-continued

SECOND COLUMN

|  | Conc. (wt. %) | Conc. (wt. %) | Conc. (wt. %) |
|---|---|---|---|
| Alkylenating Agent | 0.1 to 10 | 0.5 to 15 | 1 to 5 |
| Propionic Acid | less than 10 | 0.001 to 5 | 0.001 to 1 |
| Residue |  |  |  |
| Acrylic Acid | at least 85 | 85 to 99.9 | 95 to 99.5 |
| Acetic Acid | less than 15 | 0.1 to 10 | 0.1 to 5 |
| Water | less than 1 | less than 0.1 | less than 0.01 |
| Alkylenating Agent | less than 1 | less than 0.1 | less than 0.01 |
| Propionic Acid | less than 1 | less than 0.1 | less than 0.01 |

Returning to FIG. 2, at least a portion of stream 258 is directed to third column 254. Third column 254 separates the at least a portion of stream 258 into a distillate in line 260 and a residue in line 262. The distillate may be refluxed and the residue may be boiled up as shown. The distillate comprises a major portion of acetic acid. In one embodiment, at least a portion of line 260 is returned, either directly or indirectly, to reactor 206. The third column residue exits third column 254 in line 262 and comprises acetic acid and some acrylic acid. At least a portion of line 262 may be returned to second column 252 for further separation. In one embodiment, at least a portion of line 262 is returned, either directly or indirectly, to reactor 206. In another embodiment, at least a portion of the acetic acid-containing stream in either or both of lines 260 and 262 may be directed to an ethanol production system that utilizes the hydrogenation of acetic acid to form the ethanol. In another embodiment, at least a portion of the acetic acid-containing stream in either or both of lines 260 and 262 may be directed to a vinyl acetate system that utilizes the reaction of ethylene, acetic acid, and oxygen form the vinyl acetate. Exemplary compositional ranges for the distillate and residue of third column 254 are shown in Table 6. Components other than those listed in Table 6 may also be present in the residue and distillate.

TABLE 6

THIRD COLUMN

|  | Conc. (wt. %) | Conc. (wt. %) | Conc. (wt. %) |
|---|---|---|---|
| Distillate |  |  |  |
| Acrylic Acid | 0.01 to 10 | 0.05 to 5 | 0.1 to 1 |
| Acetic Acid | 50 to 99.9 | 70 to 99.5 | 80 to 99 |
| Water | 0.1 to 25 | 0.1 to 15 | 1 to 10 |
| Alkylenating Agent | 0.1 to 25 | 0.1 to 15 | 1 to 10 |
| Propionic Acid | less than 1 | less than 0.1 | less than 0.01 |
| Residue |  |  |  |
| Acrylic Acid | 5 to 50 | 15 to 40 | 20 to 35 |
| Acetic Acid | 50 to 95 | 60 to 80 | 65 to 75 |
| Water | 0.01 to 10 | 0.01 to 5 | 0.1 to 1 |
| Alkylenating Agent | less than 1 | 0.001 to 1 | 0.01 to 1 |
| Propionic Acid | less than 1 | less than 0.1 | less than 0.01 |

In cases where the acrylate product split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 50 kPa, less than 27 kPa, or less than 20 kPa. In terms of lower limits, the column(s) may be operated at a pressures of at least 1 kPa, e.g., at least 3 kPa or at least 5 kPa. Without being bound by theory, it has surprisingly and unexpectedly been found that be maintaining a low pressure in the columns of acrylate product split unit 234 may inhibit and/or eliminate polymerization of the acrylate products, e.g., acrylic acid, which may contribute to fouling of the column(s).

It has also been found that, surprisingly and unexpectedly, maintaining the temperature of acrylic acid-containing streams fed to acrylate product split unit 234 at temperatures below 140° C., e.g., below 130° C. or below 115° C., may inhibit and/or eliminate polymerization of acrylate products. In one embodiment, to maintain the liquid temperature at these temperatures, the pressure of the column(s) is maintained at or below the pressures mentioned above. In these cases, due to the lower pressures, the number of theoretical column stages is kept at a low level, e.g., less than 10, less than 8, less than 7, or less than 5. As such, it has surprisingly and unexpectedly been found that multiple columns having fewer trays inhibit and/or eliminate acrylate product polymerization. In contrast, a column having a higher amount of stages, e.g., more than 10 stages or more than 15 stages, would suffer from fouling due to the polymerization of the acrylate products. Thus, in a preferred embodiment, the acrylic acid split is performed in at least two, e.g., at least three, columns, each of which have less than 10 trays, e.g. less than 7 trays. These columns each may operate at the lower pressures discussed above.

Returning to FIG. 2, alkylenating agent stream 240 exits alkylenating agent split unit 232 and is directed to drying unit 236 for further separation, e.g., to further separate the water therefrom. The separation of the formaldehyde from the water may be referred to as dehydration. Drying unit 236 may comprise any suitable separation device or combination of separation devices. For example, drying unit 236 may comprise at least one column, e.g., a standard distillation column, an extractive distillation column and/or an azeotropic distillation column. In other embodiments, drying unit 236 comprises a dryer and/or a molecular sieve unit. In a preferred embodiment, drying unit 236 comprises a liquid-liquid extraction unit. In one embodiment, drying unit 236 comprises a standard distillation column as shown in FIG. 2. Of course, other suitable separation devices may be employed either alone or in combination with the devices mentioned herein.

In FIG. 2, drying unit 236 comprises fourth column 270. Drying unit 236 receives at least a portion of alkylenating agent stream in line 240 and separates same into a fourth distillate comprising water, formaldehyde, and methanol in line 272 and a fourth residue comprising mostly water in line 274. The distillate may be refluxed and the residue may be boiled up as shown. In one embodiment, at least a portion of line 272 is returned, either directly or indirectly, to reactor 206.

Exemplary compositional ranges for the distillate and residue of fourth column 270 are shown in Table 7. Components other than those listed in Table 7 may also be present in the residue and distillate.

TABLE 7

FOURTH COLUMN

|  | Conc. (wt. %) | Conc. (wt. %) | Conc. (wt. %) |
|---|---|---|---|
| Distillate |  |  |  |
| Acrylic Acid | less than 1 | less than 0.1 | less than 0.01 |
| Acetic Acid | less than 2 | 0.01 to 1 | 0.01 to 1 |
| Water | 20 to 90 | 30 to 80 | 40 to 70 |
| Alkylenating Agent | 1 to 70 | 20 to 60 | 30 to 50 |
| Methanol | 0.01 to 15 | 0.1 to 10 | 1 to 5 |
| Residue |  |  |  |
| Acrylic Acid | less than 1 | 0.001 to 1 | 0.01 to 1 |
| Acetic Acid | less than 15 | 0.1 to 10 | 0.1 to 5 |
| Water | at least 85 | 85 to 99.9 | 95 to 99.5 |
| Alkylenating Agent | less than 1 | 0.001 to 1 | 0.1 to 1 |
| Propionic Acid | less than 1 | less than 0.1 | less than 0.01 |

In cases where the drying unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa.

Returning to FIG. 2, alkylenating agent stream 272 exits drying unit 236 and is directed to methanol removal unit 238 for further separation, e.g., to further separate the methanol therefrom. Methanol removal unit 238 may comprise any suitable separation device or combination of separation devices. For example, methanol removal unit 238 may comprise at least one column, e.g., a standard distillation column, an extractive distillation column and/or an azeotropic distillation column. In one embodiment, methanol removal unit 238 comprises a liquid-liquid extraction unit. In a preferred embodiment, methanol removal unit 238 comprises a standard distillation column as shown in FIG. 2. Of course, other suitable separation devices may be employed either alone or in combination with the devices mentioned herein.

In FIG. 2, methanol removal unit 238 comprises fifth column 280. Methanol removal unit 238 receives at least a portion of line 272 and separates same into a fifth distillate comprising methanol and water in line 282 and a fifth residue comprising water and formaldehyde in line 284. The distillate may be refluxed and the residue may be boiled up (not shown). In one embodiment, at least a portion of line 284 is returned, either directly or indirectly, to reactor 206. Fifth distillate 382 may be used to form additional formaldehyde.

Exemplary compositional ranges for the distillate and residue of fifth column 280 are shown in Table 8. Components other than those listed in Table 8 may also be present in the residue and distillate.

TABLE 8

FIFTH COLUMN

|  | Conc. (wt. %) | Conc. (wt. %) | Conc. (wt. %) |
|---|---|---|---|
| Distillate |  |  |  |
| Acrylic Acid | less than 1 | less than 0.1 | less than 0.01 |
| Acetic Acid | less than 1 | less than 0.1 | less than 0.01 |
| Water | 20 to 60 | 30 to 50 | 35 to 45 |
| Alkylenating Agent | 0.1 to 25 | 0.5 to 20 | 1 to 15 |
| Methanol | 20 to 70 | 30 to 60 | 40 to 50 |
| Residue |  |  |  |
| Acrylic Acid | less than 1 | less than 0.1 | less than 0.01 |
| Acetic Acid | less than 15 | 0.1 to 10 | 0.1 to 5 |
| Water | 40 to 80 | 50 to 80 | 40 to 70 |
| Alkylenating Agent | 1 to 70 | 30 to 50 | 35 to 45 |
| Methanol | less than 15 | 0.1 to 10 | 0.1 to 5 |

In cases where the methanol removal unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa.

Figure 3:
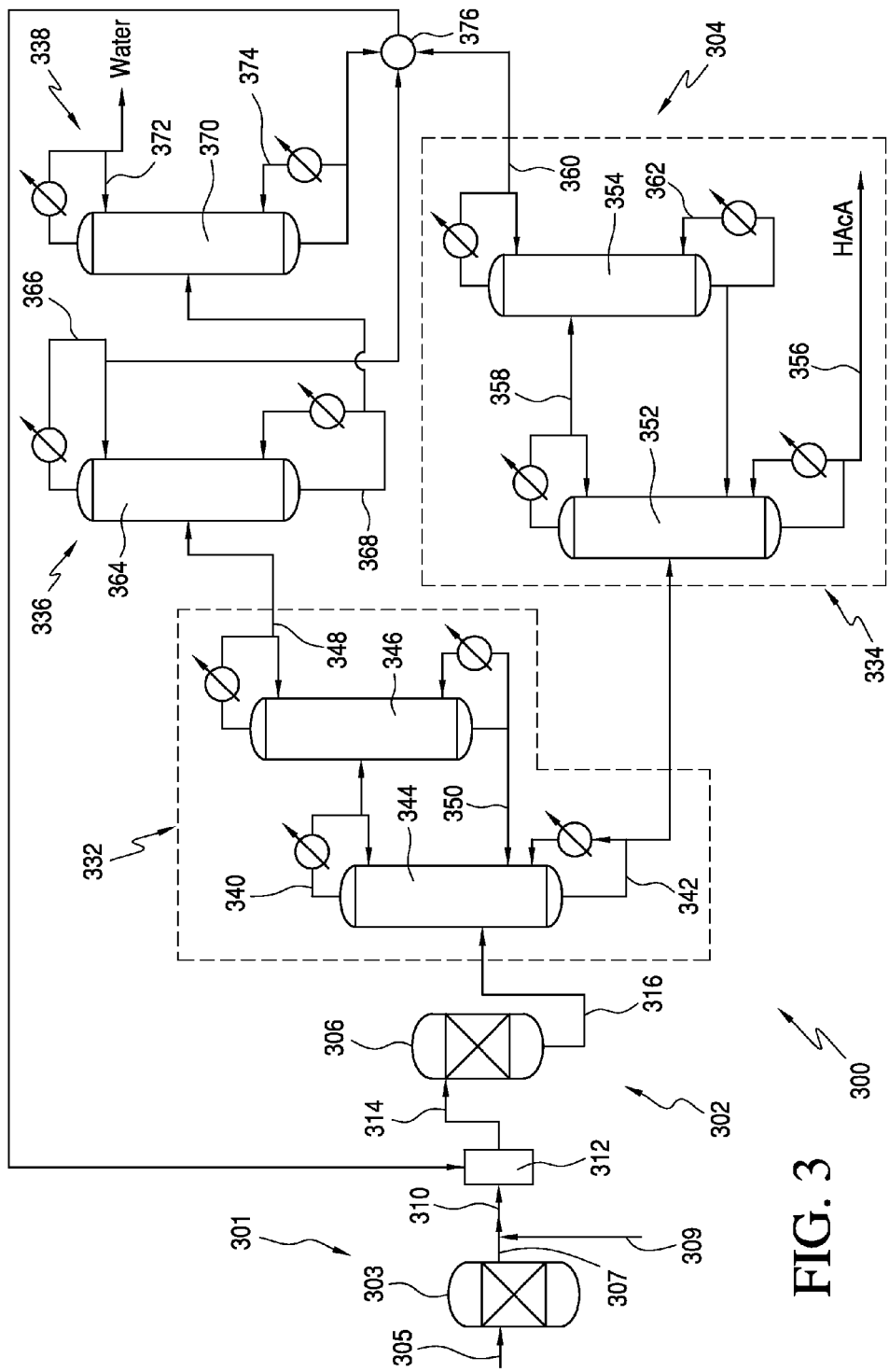
FIG. 3 is a schematic of an acrylic acid reaction/separation system in accordance with an embodiment of the present invention.

FIG. 3 shows an overview of a reaction/separation scheme in accordance with the present invention. Acrylate product system 300 comprises oxidation reaction zone 301, condensation reaction zone 302 and separation zone 304. Oxidation reaction zone comprises oxidation reactor 303, oxidation reaction gas mixture A feed 305, oxidation product gas mixture A outlet 307 and acetic acid feed 309. Condensation reaction zone 302 comprises reactor 306, condensation reaction gas mixture B feed, e.g., acetic acid and formaldehyde feed 310, and vaporizer 312. Reaction zone 302 and the components thereof function in a manner similar to reaction zone 102 of FIG. 1.

Condensation reaction zone 302 yields condensation product gas mixture B, which exits reaction zone 302 via line 316 and is directed to separation zone 304. The components of condensation product gas mixture B are discussed above.

Reaction zone 302 yields a condensation product gas mixture B, which exits reaction zone 302 via line 316 and is directed to separation zone 304. The components of condensation product gas mixture B are discussed above. Separation zone 304 comprises alkylenating agent split unit 332, acrylate product split unit 334, acetic acid split unit 336, and drying unit 338. Separation zone 304 may also comprise a light ends removal unit (not shown). For example, the light ends removal unit may comprise a condenser and/or a flasher. The light ends removal unit may be configured either upstream of the alkylenating agent split unit. Depending on the configuration, the light ends removal unit removes light ends from the crude acrylate stream, the alkylenating stream, and/or the intermediate acrylate product stream. In one embodiment, when the light ends are removed, the remaining liquid phase comprises the acrylic acid, acetic acid, alkylenating agent, and/or water.

Alkylenating agent split unit 332 may comprise any suitable separation device or combination of separation devices. For example, alkylenating agent split unit 332 may comprise a column, e.g., a standard distillation column, an extractive distillation column and/or an azeotropic distillation column. In other embodiments, alkylenating agent split unit 332 comprises a precipitation unit, e.g., a crystallizer and/or a chiller. Preferably, alkylenating agent split unit 332 comprises two standard distillation columns. In another embodiment, the alkylenating agent split is performed by contacting condensation product gas mixture B with a solvent that is immiscible with water. For example alkylenating agent split unit 332 may comprise at least one liquid-liquid extraction columns. In another embodiment, the alkylenating agent split is performed via azeotropic distillation, which employs an azeotropic agent. In these cases, the azeotropic agent may be selected from the group consisting of methyl isobutylketene, o-xylene, toluene, benzene, n-hexane, cyclohexane, p-xylene, and mixtures thereof. This listing is not exclusive and is not meant to limit the scope of the invention. In another embodiment, the alkylenating agent split is performed via a combination of distillation, e.g., standard distillation, and crystallization. Of course, other suitable separation devices may be employed either alone or in combination with the devices mentioned herein.

In FIG. 3, alkylenating agent split unit 332 comprises sixth column 344 and seventh column 346. Alkylenating agent split unit 332 receives liquid acrylate stream in line 316 and separates same into at least one alkylenating agent stream, e.g., stream 348, and at least one intermediate product stream, e.g., stream 342. Alkylenating agent split unit 332 performs an alkylenating agent split, as discussed above.

In operation, as shown in FIG. 3, condensation product gas mixture B in line 316 is directed to sixth column 344. Sixth column 344 separates condensation product gas mixture B into a distillate in line 340 and a residue in line 342. The distillate may be refluxed and the residue may be boiled up as shown. Stream 340 comprises at least 1 wt. % alkylenating agent. As such, stream 340 may be considered an alkylenating agent stream. The sixth column residue exits sixth column 344 in line 342 and comprises a significant portion of acrylate product. As such, stream 342 is an intermediate product stream. Exemplary compositional ranges for the distillate and residue of sixth column 344 are shown in Table 9. Components other than those listed in Table 9 may also be present in the residue and distillate.

TABLE 9

SIXTH COLUMN

|  | Conc. (wt. %) | Conc. (wt. %) | Conc. (wt. %) |
|---|---|---|---|
| Distillate | | | |
| Acrylic Acid | 0.1 to 20 | 1 to 10 | 1 to 5 |
| Acetic Acid | 25 to 65 | 35 to 55 | 40 to 50 |
| Water | 15 to 55 | 25 to 45 | 30 to 40 |
| Alkylenating Agent | at least 0.1 | 1 to 75 | 10 to 20 |
| Propionic Acid | <10 | 0.001 to 5 | 0.001 to 1 |
| Residue | | | |
| Acrylic Acid | at least 5 | 5 to 99 | 35 to 65 |
| Acetic Acid | less than 95 | 5 to 90 | 20 to 60 |
| Water | less than 25 | 0.1 to 10 | 0.5 to 7 |
| Alkylenating Agent | <1 | <0.5 | <0.1 |
| Propionic Acid | <10 | 0.01 to 5 | 0.01 o 1 |

In one embodiments, the first distillate comprises smaller amounts of acetic acid, e.g., less than 25 wt. %, less than 10 wt. %, e.g., less than 5 wt. % or less than 1 wt. %. In one embodiment, the first residue comprises larger amounts of alkylenating agent, e.g., In other embodiments, the intermediate acrylate product stream comprises higher amounts of alkylenating agent, e.g., greater than 1 wt. % greater than 5 wt. % or greater than 10 wt. %.

In one embodiment, polymerization inhibitors and/or anti-foam agents may be employed in the separation zone, e.g., in the units of the separation zone. The inhibitors may be used to reduce the potential for fouling caused by polymerization of acrylates. The anti-foam agents may be used to reduce potential for foaming in the various streams of the separation zone. The polymerization inhibitors and/or the anti-foam agents may be used at one or more locations in the separation zone.

Returning to FIG. 3, at least a portion of stream 340 is directed to seventh column 346. Seventh column 346 separates the at least a portion of stream 340 into a distillate in line 348 and a residue in line 350. The distillate may be refluxed and the residue may be boiled up as shown. The distillate comprises at least 1 wt. % alkylenating agent. Stream 348, like stream 340, may be considered an alkylenating agent stream. The seventh column residue exits seventh column 346 in line 350 and comprises a significant portion of acetic acid. At least a portion of line 350 may be returned to sixth column 344 for further separation. In one embodiment, at least a portion of line 350 is returned, either directly or indirectly, to reactor 306. Exemplary compositional ranges for the distillate and residue of seventh column 346 are shown in Table 10. Components other than those listed in Table 10 may also be present in the residue and distillate.

TABLE 10

SEVENTH COLUMN

|  | Conc. (wt. %) | Conc. (wt. %) | Conc. (wt. %) |
|---|---|---|---|
| Distillate | | | |
| Acrylic Acid | 0.01 to 10 | 0.05 to 5 | 0.1 to 0.5 |
| Acetic Acid | 10 to 50 | 20 to 40 | 25 to 35 |
| Water | 35 to 75 | 45 to 65 | 50 to 60 |
| Alkylenating Agent | at least 1 | 1 to 75 | 10 to 20 |
| Propionic Acid | 0.01 to 10 | 0.01 to 5 | 0.01 to 0.05 |
| Residue | | | |
| Acrylic Acid | 0.1 to 25 | 0.05 to 15 | 1 to 10 |
| Acetic Acid | 40 to 80 | 50 to 70 | 55 to 65 |
| Water | 1 to 40 | 5 to 35 | 10 to 30 |
| Alkylenating Agent | at least 1 | 1 to 75 | 10 to 20 |
| Propionic Acid | <10 | 0.001 to 5 | 0.001 to 1 |

In cases where any of the alkylenating agent split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 100 kPa, less than 80 kPa, or less than 60 kPa. In terms of lower limits, the column(s) may be operated at a pressures of at least 1 kPa, e.g., at least 20 kPa or at least 40 kPa. Without being bound by theory, it is believed that alkylenating agents, e.g., formaldehyde, may not be sufficiently volatile at lower pressures. Thus, maintenance of the separation unit pressures, e.g., column pressures, at low levels surprisingly and unexpectedly provides for efficient separation operations. In addition, it has surprisingly and unexpectedly been found that maintenance of these low pressures may inhibit and/or eliminate polymerization of the acrylate products, e.g., acrylic acid, which may contribute to fouling of the column(s). Also, it has surprisingly and unexpectedly been found that by maintaining the temperature of the units, e.g., columns, at a low level (as discussed below), may inhibit and/or eliminate polymerization of the acrylate products.

In one embodiment, the alkylenating agent split is achieved via one or more liquid-liquid extraction units. Preferably, the one or more liquid-liquid extraction units employ one or more extraction agents. Multiple liquid-liquid extraction units may be employed to achieve the alkylenating agent split. Any suitable liquid-liquid extraction devices used for multiple equilibrium stage separations may be used. Also, other separation devices, e.g., traditional columns, may be employed in conjunction with the liquid-liquid extraction unit(s).

In one embodiment (not shown), condensation product gas mixture B is fed to a liquid-liquid extraction column where condensation product gas mixture B is contacted with an extraction agent, e.g., an organic solvent. The liquid-liquid extraction column extracts the acids, e.g., acrylic acid and acetic acid, from condensation product gas mixture B. An aqueous stage comprising water, alkylenating agent, and some acetic acid exits the liquid-liquid extraction unit. Small amounts of acylic acid may also be present in the aqueous stream. The aqueous phase may be further treated and/or recycled. An organic phase comprising acrylic acid, acetic acid, and the extraction agent also exits the liquid-liquid extraction unit. The organic phase may also comprise water and formaldehyde. The acrylic acid may be separated from the organic phase and collected as product. The acetic acid may be separated then recycled and/or used elsewhere. The solvent may be recovered and recycled to the liquid-liquid extraction unit.

The inventive process further comprises the step of separating the intermediate acrylate product stream to form a finished acrylate product stream and a first finished acetic acid stream. The finished acrylate product stream comprises acrylate product(s) and the first finished acetic acid stream comprises acetic acid. The separation of the acrylate products from the intermediate product stream to form the finished acrylate product may be referred to as the "acrylate product split."

Returning to FIG. 3, intermediate product stream 342 exits alkylenating agent split unit 332 and is directed to acrylate product split unit 334 for further separation, e.g., to further separate the acrylate products therefrom. Acrylate product split unit 334 may comprise any suitable separation device or combination of separation devices. For example, acrylate product split unit 334 may comprise at least one column, e.g., a standard distillation column, an extractive distillation column and/or an azeotropic distillation column. In other embodiments, acrylate product split unit 334 comprises a precipitation unit, e.g., a crystallizer and/or a chiller. Preferably, acrylate product split unit 334 comprises two standard distillation columns as shown in FIG. 3. In another embodiment, acrylate product split unit 334 comprises a liquid-liquid extraction unit. Of course, other suitable separation devices may be employed either alone or in combination with the devices mentioned herein.

In FIG. 3, acrylate product split unit 334 comprises eighth column 352 and ninth column 354. Acrylate product split unit 334 receives at least a portion of purified acrylic product stream in line 342 and separates same into finished acrylate product stream 356 and at least one acetic acid-containing stream. As such, acrylate product split unit 334 may yield the finished acrylate product.

As shown in FIG. 3, at least a portion of purified acrylic product stream in line 342 is directed to eighth column 352. Eighth column 352 separates the purified acrylic product stream to form eighth distillate, e.g., line 358, and eighth residue, which is the finished acrylate product stream, e.g., line 356. The distillate may be refluxed and the residue may be boiled up as shown.

Stream 358 comprises acetic acid and some acrylic acid. The eighth column residue exits eighth column 352 in line 356 and comprises a significant portion of acrylate product. As such, stream 356 is a finished product stream. Exemplary compositional ranges for the distillate and residue of eighth column 352 are shown in Table 11. Components other than those listed in Table 11 may also be present in the residue and distillate.

TABLE 11

EIGHTH COLUMN

| | Conc. (wt. %) | Conc. (wt. %) | Conc. (wt. %) |
|---|---|---|---|
| Distillate | | | |
| Acrylic Acid | 0.1 to 40 | 1 to 30 | 5 to 30 |
| Acetic Acid | 60 to 99 | 70 to 90 | 75 to 85 |
| Water | 0.1 to 25 | 0.1 to 10 | 1 to 5 |
| Alkylenating Agent | less than 1 | 0.001 to 1 | 0.1 to 1 |
| Propionic Acid | <10 | 0.001 to 5 | 0.001 to 1 |
| Residue | | | |
| Acrylic Acid | at least 85 | 85 to 99.9 | 95 to 99.5 |
| Acetic Acid | less than 15 | 0.1 to 10 | 0.1 to 5 |
| Water | less than 1 | less than 0.1 | less than 0.01 |
| Alkylenating Agent | less than 1 | 0.001 to 1 | 0.1 to 1 |
| Propionic Acid | 0.1 to 10 | 0.1 to 5 | 0.5 to 3 |

Returning to FIG. 3, at least a portion of stream 358 is directed to ninth column 354. Ninth column 354 separates the at least a portion of stream 358 into a distillate in line 360 and a residue in line 362. The distillate may be refluxed and the residue may be boiled up as shown. The distillate comprises a major portion of acetic acid. In one embodiment, at least a portion of line 360 is returned, either directly or indirectly, to reactor 306. The ninth column residue exits ninth column 354 in line 362 and comprises acetic acid and some acrylic acid. At least a portion of line 362 may be returned to eighth column 352 for further separation. In one embodiment, at least a portion of line 362 is returned, either directly or indirectly, to reactor 306. In another embodiment, at least a portion of the acetic acid-containing stream in either or both of lines 360 and 362 may be directed to an ethanol production system that utilizes the hydrogenation of acetic acid form the ethanol. In another embodiment, at least a portion of the acetic acid-containing stream in either or both of lines 360 and 362 may be directed to a vinyl acetate system that utilizes the reaction of ethylene, acetic acid, and oxygen form the vinyl acetate. Exemplary compositional ranges for the distillate and residue of ninth column 354 are shown in Table 12. Components other than those listed in Table 12 may also be present in the residue and distillate.

TABLE 12

NINTH COLUMN

| | Conc. (wt. %) | Conc. (wt. %) | Conc. (wt. %) |
|---|---|---|---|
| Distillate | | | |
| Acrylic Acid | 0.01 to 10 | 0.05 to 5 | 0.1 to 1 |
| Acetic Acid | 50 to 99.9 | 70 to 99.5 | 80 to 99 |
| Water | 0.1 to 25 | 0.1 to 15 | 1 to 10 |
| Alkylenating Agent | less than 10 | 0.001 to 5 | 0.01 to 5 |
| Propionic Acid | 0.0001 to 10 | 0.001 to 5 | 0.001 to 0.05 |

TABLE 12-continued

NINTH COLUMN

| | Conc. (wt. %) | Conc. (wt. %) | Conc. (wt. %) |
|---|---|---|---|
| Residue | | | |
| Acrylic Acid | 5 to 50 | 15 to 40 | 20 to 35 |
| Acetic Acid | 50 to 95 | 60 to 80 | 65 to 75 |
| Water | 0.01 to 10 | 0.01 to 5 | 0.1 to 1 |
| Alkylenating Agent | less than 1 | 0.001 to 1 | 0.1 to 1 |
| Propionic Acid | <10 | 0.001 to 5 | 0.001 to 1 |

In cases where the acrylate product split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 50 kPa, less than 27 kPa, or less than 20 kPa. In terms of lower limits, the column(s) may be operated at a pressures of at least 1 kPa, e.g., at least 3 kPa or at least 5 kPa. Without being bound by theory, it has surprisingly and unexpectedly been found that be maintaining a low pressure in the columns of acrylate product split unit 334 may inhibit and/or eliminate polymerization of the acrylate products, e.g., acrylic acid, which may contribute to fouling of the column(s).

It has also been found that, surprisingly and unexpectedly, maintaining the temperature of acrylic acid-containing streams fed to acrylate product split unit 334 at temperatures below 140° C., e.g., below 130° C. or below 115° C., may inhibit and/or eliminate polymerization of acrylate products. In one embodiment, to maintain the liquid temperature at these temperatures, the pressure of the column(s) is maintained at or below the pressures mentioned above. In these cases, due to the lower pressures, the number of theoretical column trays is kept at a low level, e.g., less than 10, less than 8, less than 7, or less than 5. As such, it has surprisingly and unexpectedly been found that multiple columns having fewer trays inhibit and/or eliminate acrylate product polymerization. In contrast, a column having a higher amount of trays, e.g., more than 10 trays or more than 15 trays, would suffer from fouling due to the polymerization of the acrylate products. Thus, in a preferred embodiment, the acrylic acid split is performed in at least two, e.g., at least three, columns, each of which have less than 10 trays, e.g. less than 7 trays. These columns each may operate at the lower pressures discussed above.

The inventive process further comprises the step of separating an alkylenating agent stream to form a purified alkylenating stream and a purified acetic acid stream. The purified alkylenating agent stream comprises a significant portion of alkylenating agent, and the purified acetic acid stream comprises acetic acid and water. The separation of the alkylenating agent from the acetic acid may be referred to as the "acetic acid split."

Returning to FIG. 3, alkylenating agent stream 348 exits alkylenating agent split unit 332 and is directed to acetic acid split unit 336 for further separation, e.g., to further separate the alkylenating agent and the acetic acid therefrom. Acetic acid split unit 336 may comprise any suitable separation device or combination of separation devices. For example, acetic acid split unit 336 may comprise at least one column, e.g., a standard distillation column, an extractive distillation column and/or an azeotropic distillation column. In other embodiments, acetic acid split unit 336 comprises a precipitation unit, e.g., a crystallizer and/or a chiller. Preferably, acetic acid split unit 336 comprises a standard distillation column as shown in FIG. 3. In another embodiment, acetic acid split unit 336 comprises a liquid-liquid extraction unit. Of course, other suitable separation devices may be employed either alone or in combination with the devices mentioned herein.

In FIG. 3, acetic acid split unit 336 comprises tenth column 364. Acetic acid split unit 336 receives at least a portion of alkylenating agent stream in line 348 and separates same into a tenth distillate comprising alkylenating agent in line 366, e.g., a purified alkylenating stream, and a tenth residue comprising acetic acid in line 368, e.g., a purified acetic acid stream. The distillate may be refluxed and the residue may be boiled up as shown. In one embodiment, at least a portion of line 366 and/or line 368 are returned, either directly or indirectly, to reactor 306. At least a portion of stream in line 368 may be further separated. In another embodiment, at least a portion of the acetic acid-containing stream in line 368 may be directed to an ethanol production system that utilizes the hydrogenation of acetic acid form the ethanol. In another embodiment, at least a portion of the acetic acid-containing stream in line 368 may be directed to a vinyl acetate system that utilizes the reaction of ethylene, acetic acid, and oxygen form the vinyl acetate.

The stream in line 366 comprises alkylenating agent and water. The stream in line 368 comprises acetic acid and water. Exemplary compositional ranges for the distillate and residue of tenth column 364 are shown in Table 13. Components other than those listed in Table 13 may also be present in the residue and distillate.

TABLE 13

TENTH COLUMN

| | Conc. (wt. %) | Conc. (wt. %) | Conc. (wt. %) |
|---|---|---|---|
| Distillate | | | |
| Acrylic Acid | less than 1 | 0.001 to 5 | 0.001 to 1 |
| Acetic Acid | less than 1 | 0.001 to 5 | 0.001 to 1 |
| Water | 40 to 80 | 50 to 70 | 55 to 65 |
| Alkylenating Agent | 20 to 60 | 30 to 50 | 35 to 45 |
| Propionic Acid | less than 1 | 0.001 to 5 | 0.001 to 1 |
| Residue | | | |
| Acrylic Acid | less than 1 | 0.01 to 5 | 0.1 to 1 |
| Acetic Acid | 25 to 65 | 35 to 55 | 40 to 50 |
| Water | 35 to 75 | 45 to 65 | 50 to 60 |
| Alkylenating Agent | less than 1 | 0.01 to 5 | 0.1 to 1 |
| Propionic Acid | less than 1 | 0.01 5 | 0.02 1 |

In cases where the acetic acid split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa.

The inventive process further comprises the step of separating the purified acetic acid stream to form a second finished acetic acid stream and a water stream. The second finished acetic acid stream comprises a major portion of acetic acid, and the water stream comprises mostly water. The separation of the acetic from the water may be referred to as dehydration.

Returning to FIG. 3, tenth residue 368 exits acetic acid split unit 336 and is directed to drying unit 338 for further separation, e.g., to remove water from the acetic acid. Drying unit 338 may comprise any suitable separation device or combination of separation devices. For example, drying unit 338 may comprise at least one column, e.g., a standard distillation column, an extractive distillation column and/or an azeotropic distillation column. In other embodiments, drying unit 338 comprises a dryer and/or a molecular sieve unit. In a preferred embodiment, drying unit 338 comprises a liquid-liquid extraction unit. In one embodiment, drying unit 338 comprises a standard distillation column as shown in FIG. 3. Of course, other suitable separation devices may be employed either alone or in combination with the devices mentioned herein.

In FIG. 3, drying unit 338 comprises eleventh column 370. Drying unit 338 receives at least a portion of finished acetic acid stream in line 368 and separates same into an eleventh distillate comprising a major portion of water in line 372 and an eleventh residue comprising acetic acid and small amounts of water in line 374. The distillate may be refluxed and the residue may be boiled up as shown. In one embodiment, at least a portion of line 374 is returned, either directly or indirectly, to reactor 306. In another embodiment, at least a portion of the acetic acid-containing stream in line 374 may be directed to an ethanol production system that utilizes the hydrogenation of acetic acid form the ethanol. In another embodiment, at least a portion of the acetic acid-containing stream in line 374 may be directed to a vinyl acetate system that utilizes the reaction of ethylene, acetic acid, and oxygen form the vinyl acetate.

Exemplary compositional ranges for the distillate and residue of eleventh column 370 are shown in Table 14. Components other than those listed in Table 14 may also be present in the residue and distillate.

TABLE 14

ELEVENTH COLUMN

| | Conc. (wt. %) | Conc. (wt. %) | Conc. (wt. %) |
|---|---|---|---|
| Distillate | | | |
| Acrylic Acid | less than 1 | 0.001 to 5 | 0.001 to 1 |
| Acetic Acid | less than 1 | 0.01 to 5 | 0.01 to 1 |
| Water | 90 to 99.9 | 95 to 99.9 | 95 to 99.5 |
| Alkylenating Agent | less than 1 | 0.01 to 5 | 0.01 to 1 |
| Propionic Acid | less than 10 | 0.001 to 5 | 0.001 to 1 |
| Residue | | | |
| Acrylic Acid | less than 1 | 0.01 to 5 | 0.01 to 1 |
| Acetic Acid | 75 to 99.9 | 85 to 99.5 | 90 to 99.5 |
| Water | 25 to 65 | 35 to 55 | 40 to 50 |
| Alkylenating Agent | less than 1 | less than 0.001 | less than 0.0001 |
| Propionic Acid | less than 10 | 0.001 to 5 | 0.01 to 1 |

In cases where the drying unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa. FIG. 3 also shows tank 376, which, collects at least one of the process streams prior to recycling same to reactor 306. Tank 376 is an optional feature. The various purge streams that may, alternatively, be recycled directly to reactor 306 without being collected in tank 376.

The following embodiments are within the scope of the present invention.

1. A process for preparing acrylic acid from methanol and acetic acid, which comprises the following measures:

A stream of a reaction gas input mixture A comprising the methanol and molecular oxygen reactants and at least one inert diluent gas other than steam is directed through a first reaction zone A, which is charged with at least one oxidation catalyst A. The reaction gas input mixture may comprise oxygen and methanol, preferably in a molar ratio of at least 1, e.g., at least 2, at least 5, or at least 10. In the course of passage through reaction zone A, methanol present in the reaction gas input mixture A is oxidized under heterogeneous catalysis to form formaldehyde and steam, which exit as product gas mixture A. Product gas mixture A comprises formaldehyde, steam, and at least one inert diluent gas other than steam. The oxidation reaction may, in some embodiments, be conducted with or without excess molecular oxygen. Product gas mixture A leaves reaction zone A. In one embodiment, molecular oxygen and/or further inert diluent gas are supplied to the reaction gas mixture A flowing through reaction zone A. Product gas mixture A may, in some embodiments, comprise methanol, e.g., unconverted methanol.

Optionally, the stream of product gas mixture A leaving reaction zone A may be fed to a separation zone T* and any unconverted methanol still present in product gas mixture A in separation zone T* may be removed from product gas mixture A to leave a formaldehyde-comprising product gas mixture A*. A stream of product gas mixture A* leaves reaction zone A.

The process may form a stream of a reaction gas input mixture B from the product gas mixture A. The reaction gas input mixture B may comprise acetic acid, steam, at least one inert diluent gas other than steam and formaldehyde, with or without molecular oxygen. In one embodiment, the molar amount of acetic acid, $n_{HAc}$, present in the reaction gas input mixture B is greater than the molar amount of formaldehyde, $n_{Fd}$, present in the reaction gas input mixture B. The reaction gas input mixture B may be formed by combining an acetic acid stream and at least a portion of product gas mixture A.

The reaction gas input mixture B is passed through a second reaction zone B, which is charged with at least one aldol condensation catalyst B. Formaldehyde present in reaction gas input mixture B, as it flows through reaction zone B, is condensed with acetic acid present in reaction gas input mixture B (preferably under heterogeneous catalysis) to form product gas mixture B comprising acrylic acid and water. In one embodiment, the reaction gas mixture B comprises acetic acid and formaldehyde in a molar ratio ranging from 1 to 10, e.g., from 1 to 8 or from 1 to 5. Product gas mixture B comprises acrylic acid, acetic acid, steam and at least one inert diluent gas other than steam, optionally with or without molecular oxygen. The product gas mixture B leaves reaction zone B. In one embodiment, it optionally is possible to supply further molecular oxygen and/or further inert diluent gas to the reaction gas mixture B.

The stream of product gas mixture B leaving reaction zone B is fed to a separation zone T and separated in separation zone T into at least three streams X, Y and Z. The acrylic acid flow present in stream X is greater than the acrylic acid flow present in streams Y and Z together. The acetic acid flow present in stream Y is greater than the acetic acid flow present in streams X and Z together. The flow of inert diluent gas other than steam present in stream Z is greater than the flow of inert diluent gas other than steam present in streams X and Y together. Stream Y may be recycled into reaction zone B and used to obtain reaction gas input mixture B.

2. The process according to embodiment 1, wherein methanol removed in separation zone T* is recycled into reaction zone A to obtain reaction gas input mixture A.

3. The process according to embodiment 1 or 2, wherein the methanol is removed by rectification in separation zone T*.

4. The process according to any of embodiments 1 to 3, wherein the at least one oxidation catalyst A has a catalytically active material which comprises at least elemental silver.

5. The process according to embodiment 4, wherein the purity of the elemental silver is .gtoreq.99.7% by weight.

6. The process according to embodiment 4, wherein the purity of the elemental silver is ≥99.9% or ≥99.99% by weight.

7. The process according to any of embodiments 4 to 6, wherein the at least one oxidation catalyst A comprises silver crystals who longest dimension is in the range from 0.1 to 5 mm.

8. The process according to embodiment 7, wherein the silver crystals have been coated with a porous layer of oxidic material of at least one of the elements Al, Si, Zr and Ti, the thickness of which is in the range from 0.3 to 10 .mu.m.

9. The process according to any of embodiments 4 to 8, wherein the methanol content of reaction gas input mixture A is at least 5% by volume.

10. The process according to embodiment 9, wherein the methanol content of reaction gas input mixture A is not more than 60% by volume.

11. The process according to any of embodiments 4 to 8, wherein the methanol content of reaction gas input mixture A is 15 to 50% by volume.

12. The process according to any of embodiments 4 to 8, wherein the methanol content of reaction gas input mixture A is 20 to 40% by volume or 20 to 30% by volume.

13. The process according to any of embodiments 4 to 12, wherein reaction gas input mixture A comprises the molecular oxygen in a molar amount $n_o$ and the methanol in a molar amount $n_{Me}$, and the $n_o:n_{Me}$ ratio is less than 1.

14. The process according to embodiment 13, wherein $n_o:n_{Me}$ is 0.1 to 0.8 or 0.2 to 0.6.

15. The process according to any of embodiments 4 to 14, wherein $n_o:n_{Me}$ is 0.3 to 0.5.

16. The process according to any of embodiments 4 to 15, wherein reaction gas input mixture A comprises 0 to 50% by volume of $H_2O$.

17. The process according to embodiment 16, wherein reaction gas input mixture A comprises 15 to 35% by volume or 20 to 30% by volume of $H_2O$.

18. The process according to any of embodiments 4 to 17, wherein reaction gas input mixture A comprises $N_2$ as at least one inert diluent gas other than steam.

19. The process according to embodiment 18, wherein reaction gas input mixture A comprises 20 to 80% by volume of $N_2$.

20. The process according to embodiment 18 or 19, wherein reaction gas input mixture A comprises 30 to 70% by volume of $N_2$.

21. The process according to any of embodiments 18 to 20, wherein reaction gas input mixture A comprises 40 to 60% by volume of $N_2$.

22. The process according to any of embodiments 4 to 21, wherein the methanol is oxidized to formaldehyde and water in reaction zone A at a reaction temperature in the range from 400 to 800° C.

23. The process according to any of embodiments 4 to 22, wherein the methanol is oxidized to formaldehyde and water in reaction zone A at a reaction temperature in the range from 500 to 800° C.

24. The process according to any of embodiments 4 to 22, wherein the methanol is oxidized to formaldehyde and water in reaction zone A at a reaction temperature in the range from 450 to 650° C., or from 500 to 600° C.

25. The process according to any of embodiments 4 to 22, wherein the methanol is oxidized to formaldehyde and water in reaction zone A at a reaction temperature in the range from 600 to 750° C.

26. The process according to any of embodiments 4 to 25, wherein the methanol is oxidized to formaldehyde and water in reaction zone A at a working pressure in the range from $10^3$ to $10^6$ Pa or from $10^4$ to $2\times10^5$ Pa.

27. The process according to any of embodiments 1 to 3, wherein the at least one oxidation catalyst A has a catalytically active material which is a mixed oxide which has at least one transition metal in the oxidized state.

28. The process according to embodiment 27, wherein the at least one transition metal comprises Mo and/or V.

29. The process according to embodiment 27, wherein the at least one transition metal comprises Mo and Fe.

30. The process according to embodiment 27, wherein the catalytically active material is a mixed oxide of the general formula I

$$[Fe_2(MoO_4)_3]_1[M^1_mO_n]_q \qquad (I)$$

in which the variables are each defined as follows:

$M^1$ is Mo and/or Fe, or

Mo and/or Fe and, based on the total molar amount of Mo and Fe, a total molar amount of up to 10 mol % (e.g. 0.01 to 10 mol %, or 0.1 to 10 mol %), preferably to an extent of not more than 5 mol %, of one or more elements from the group consisting of Ti, Sb, Sn, Ni, Cr, Ce, Al, Ca, Mg, V, Nb, Ag, Mn, Cu, Co, Si, Na, K, Tl, Zr, W, Ir, Ta, As, P and B, q is 0 to 5, m is 1 to 3, n is 1 to 6.

31. The process according to embodiment 30, wherein q=0.5 to 3.

32. The process according to embodiment 30 or 31, wherein q=1 to 2.

33. The process according to any of embodiments 30 to 32, wherein $M^1$ is Mo, m is 1 and n is 3.

34. The process according to any of embodiments 30 to 33, wherein $M^1$ is Fe, m is 2 and n is 3.

35. The process according to any of embodiments 30 to 34, wherein less than 50 mol % of the Fe present in the mixed oxide I is present in the +2 oxidation state.

36. The process according to any of embodiments 30 to 34, wherein less than 20 mol % of the Fe present in the mixed oxide I is present in the +2 oxidation state.

37. The process according to any of embodiments 30 to 34, wherein less than 10 mol % of the Fe present in the mixed oxide I is present in the +2 oxidation state.

38. The process according to any of embodiments 30 to 34, wherein the entire amount of the Fe present in the mixed oxide I is present in the +3 oxidation state.

39. The process according to any of embodiments 30 to 38, wherein the ratio $n_{Mo}:n_{Fe}$, formed from the molar amount of Mo present in the mixed oxide I and the molar amount of Fe present in the same mixed oxide I, is 1:1 to 5:1.

40. The process according to any of embodiments 30 to 38, wherein the catalytically active material can be represented in a formal sense as a mixture of $MoO_3$ and $Fe_2O_3$, wherein the $MoO_3$ content of the mixture is 65 to 95% by weight and the $Fe_2O_3$ content of the mixture is 5 to 35% by weight.

41. The process according to any of embodiments 27 to 40, wherein the at least one oxidation catalyst A is an unsupported catalyst.

42. The process according to embodiment 41, wherein the geometry of the unsupported catalyst is selected from the group consisting of sphere, ring and solid cylinder.

43. The process according to embodiment 42, wherein the longest dimension of the unsupported catalyst is 1 to 10 mm.

44. The process according to embodiment 41, wherein the unsupported catalyst has the geometry of a ring with an external diameter of 3 to 10 mm, a height of 1 to 10 mm and an internal diameter of 1 to 8 mm.

45. The process according to embodiment 44, wherein the ring has a wall thickness of 1 to 3 mm.

46. The process according to any of embodiments 27 to 40, wherein the at least one oxidation catalyst A is an eggshell catalyst which has the catalytically active mixed oxide as an eggshell applied to the surface of an inert shaped support body.

47. The process according to embodiment 46, wherein the shaped support body is a sphere or a ring.

48. The process according to embodiment 47, wherein the longest dimension of the shaped support body is 1 to 10 mm.

49. The process according to embodiment 46, wherein the inert shaped support body is a ring with a length of 2 to 10 mm, an external diameter of 4 to 10 mm and a wall thickness of 1 to 4 mm.

50. The process according to any of embodiments 46 to 49, wherein the inert shaped support body is composed of steatite.

51. The process according to any of embodiments 46 to 50, wherein the eggshell of catalytically active mixed oxide has a thickness of 10 to 2000 µm, or 10 to 500 µm, or 100 to 500 µm, or 200 to 300 µm.

52. The process according to any of embodiments 27 to 51, wherein reaction gas input mixture A comprises not more than 15% by volume of methanol.

53. The process according to any of embodiments 27 to 51, wherein reaction gas input mixture A comprises not more than 11% by volume of methanol.

54. The process according to any of embodiments 27 to 53, wherein reaction gas input mixture A comprises 2 to 10% by volume of methanol.

55. The process according to any of embodiments 27 to 54, wherein reaction gas input mixture A comprises 6 to 9% by volume of methanol.

56. The process according to any of embodiments 27 to 55, wherein reaction gas input mixture A comprises the molecular oxygen in a molar amount $n_o$ and the methanol in a molar amount $n_{Me}$, and the $n_o:n_{Me}$ ratio is at least 1 or greater than 1.

57. The process according to embodiment 56, wherein the $n_o:n_{Me}$ ratio is 1.1 to 5.

58. The process according to embodiment 56 or 57, wherein the $n_o:n_{Me}$ ratio is 1.5 to 3.5.

59. The process according to any of embodiments 27 to 58, wherein reaction gas input mixture A comprises $N_2$ as at least one inert diluent gas other than steam.

60. The process according to embodiment 59, wherein reaction gas input mixture A comprises 70 to 95% by volume of $N_2$.

61. The process according to any of embodiments 27 to 60, wherein reaction gas input mixture A comprises 0 to 20% by volume of $H_2O$.

62. The process according to embodiment 61, wherein reaction gas input mixture A comprises 0.1 to 10% by volume of $H_2O$.

63. The process according to embodiment 61 or 62, wherein reaction gas input mixture A comprises 0.2 to 7% by volume of $H_2O$.

64. The process according to any of embodiments 60 to 62, wherein reaction gas input mixture A comprises 0.5 to 5% by volume of $H_2O$.

65. The process according to any of embodiments 27 to 64, wherein the methanol is oxidized to formaldehyde and water in reaction zone A at a reaction temperature in the range from 250 to 500° C.

66. The process according to embodiment 65, wherein the methanol is oxidized to formaldehyde and water in reaction zone A at a reaction temperature in the range from 250 to 400° C.

67. The process according to any of embodiments 27 to 66, wherein the methanol is oxidized to formaldehyde and water in reaction zone A at a working pressure in the range from $10^3$ to $10^6$ Pa or from $10^4$ to $2 \times 10^5$ Pa.

68. The process according to embodiment 67, wherein a portion of the stream Y is recycled into reaction zone A to obtain reaction gas input mixture A.

69. The process according to any of embodiments 1 to 68, wherein the acetic acid present in the at least one further stream is acetic acid obtained by homogeneous catalysis catalyzed carbonylation of methanol in the liquid phase.

70. The process according to embodiment 69, wherein the catalyst comprises Rh in combination with HI and $CH_3I$.

71. The process according to embodiment 69 or 70, wherein the acetic acid present in the at least one further stream is acetic acid removed by rectification from the product mixture of the homogeneously catalyzed carbonylation of methanol to acetic acid in the liquid phase.

72. The process according to any of embodiments 1 to 68, wherein the at least one further stream comprising acetic acid is the product gas mixture of a heterogeneously catalyzed gas phase carbonylation of methanol to acetic acid in the absence of halogenated compounds.

73. The process according to any of embodiments 1 to 72, wherein the reaction temperature in reaction zone B is 200 to 400° C.

74. The process according to any of embodiments 1 to 72, wherein the reaction temperature in reaction zone B is 280 to 380° C.

75. The process according to any of embodiments 1 to 72, wherein the reaction temperature in reaction zone B is 300 to 370° C.

76. The process according to any of embodiments 1 to 75, wherein the working pressure in reaction zone B is $1.2 \times 10^5$ Pa to $50 \times 10^5$ Pa.

77. The process according to any of embodiments 1 to 76, wherein the formaldehyde content of reaction gas input mixture B is 0.5 to 10% by volume.

78. The process according to any of embodiments 1 to 76, wherein the formaldehyde content of reaction gas input mixture B is 0.5 to 7% by volume.

79. The process according to any of embodiments 1 to 76, wherein the formaldehyde content of reaction gas input mixture B is 1 to 5% by volume.

80. The process according to any of embodiments 1 to 79, wherein reaction gas input mixture B comprises acetic acid in a molar amount $n_{me}$ and formaldehyde in a molar amount $n_{Fd}$, and the $n_{HAc}:n_{Fd}$ ratio is greater than 1 and ≤10.

81. The process according to embodiment 80, wherein the $n_{HAc}:n_{Fd}$ ratio is 1.1 to 5.

82. The process according to embodiment 80, wherein the $n_{HAc}:n_{Fd}$ ratio is 1.5 to 3.5.

83. The process according to any of embodiments 1 to 82, wherein the acetic acid content of reaction gas input mixture B is 1.5 to 20% by volume.

84. The process according to any of embodiments 1 to 82, wherein the acetic acid content of reaction gas input mixture B is 2 to 15% by volume.

85. The process according to any of embodiments 1 to 82, wherein the acetic acid content of reaction gas input mixture B is 3 to 10% by volume.

86. The process according to any of embodiments 1 to 85, wherein the molecular oxygen content of reaction gas input mixture B is 0.5 to 5% by volume.

87. The process according to any of embodiments 1 to 85, wherein the molecular oxygen content of reaction gas input mixture B is 2 to 5% by volume.

88. The process according to any of embodiments 1 to 87, wherein the steam content of reaction gas input mixture B does not exceed 30% by volume and is not less than 0.5% by volume.

89. The process according to any of embodiments 1 to 87, wherein the steam content of reaction gas input mixture B does not exceed 20% by volume and is not less than 1% by volume.

90. The process according to any of embodiments 1 to 87, wherein the steam content of reaction gas input mixture B is 0.5 to 15% by volume or 1 to 10% by volume.

91. The process according to any of embodiments 1 to 90, wherein the content of inert diluent gas other than steam in reaction gas input mixture B is at least 30% by volume or at least 40% by volume.

92. The process according to any of embodiments 1 to 90, wherein the content of inert diluent gas other than steam in reaction gas input mixture B is at least 50% by volume.

93. The process according to any of embodiments 1 to 92, wherein reaction gas input mixture B comprises, as at least one inert diluent gas other than steam, at least 30% by volume or at least 40% by volume of $N_2$.

94. The process according to any of embodiments 1 to 92, wherein reaction gas input mixture B comprises, as at least one inert diluent gas other than steam, at least 50% by volume of $N_2$.

95. The process according to any of embodiments 1 to 94, wherein the at least one aldol condensation catalyst B is a zeolite with anionic structural charge, on whose inner and outer surfaces at least one cation type from the group of the alkali metal ions and alkaline earth metal ions is present, in order to neutralize the negative structural charge.

96. The process according to any of embodiments 1 to 94, wherein the at least one aldol condensation catalyst B is hydroxide from the group consisting of alkali metal hydroxides, alkaline earth metal hydroxides and aluminum hydroxide applied to amorphous silicon dioxide.

97. The process according to embodiment 96, wherein the hydroxide applied to the amorphous silicon dioxide is KOH, NaOH, $Ca(OH)_2$ or $Mg(OH)_2$.

98. The process according to any of embodiments 1 to 94, wherein the at least one aldol condensation catalyst B is a catalyst which comprises a), at least one oxide of at least one of the elements Si, Al, Ti, Zr, Cd, Sn, Ga, Y and La and/or zeolite, and b), at least one oxide selected from boron oxide and phosphorus oxide, and optionally c), one or more than one oxide of at least one of the elements V, Cr, Co, Ni, Mo and Pb and/or more than one heteropolyacid with at least one poly atom selected from V, Mo and W.

99. The process according to embodiment 98, wherein the at least one aldol condensation catalyst B comprises 1 to 50% by weight of boron oxide, or 1 to 50% by weight of phosphorus oxide, or 1 to 50% by weight of boron oxide and phosphorus oxide, where the boron oxide, based on the amount of B present, is always calculated as $B_2O_3$ and the phosphorus oxide, based on the amount of P present, is always calculated as $P_2O_5$.

100. The process according to any of embodiments 1 to 94, wherein the at least one aldol condensation catalyst B has a catalytically active material which is a vanadium-phosphorus oxide or a vanadium-phosphorus oxide doped with elements other than vanadium and phosphorus.

101. The process according to embodiment 100, wherein the catalytically active material is a multielement oxide active material of the general formula II

   (II)

in which the variables are each defined as follows:
$X^1$=Mo, Bi, Co, Ni, Si, Zn, Hf, Zr, Ti, Cr, Mn, Cu, B, Sn and/or Nb,
$X^2$=Li, K, Na, Rb, Cs and/or Tl,
b is 0.9 to 2.0
c is ≥0 to 0.1
d is ≥0 to 0.1,
e is ≥0 to 0.1, and
n is the stoichiometric coefficient of the element oxygen, which is determined by the stoichiometric coefficients of the non-oxygen elements and the charge numbers thereof in II.

102. The process according to embodiment 101, wherein $X^1$=Nb, Mo, Zn and/or Hf.

103. The process according to embodiment 101 or 102, wherein b is 0.9 to 1.5.

104. The process according to embodiment 101 or 102, wherein b is 0.9 to 1.2.

105. The process according to any of embodiments 101 to 104, wherein $X^1$=Mo.

106. The process according to any of embodiments 101 to 105, wherein c is 0.005 to 0.1.

107. The process according to any of embodiments 101 to 105, wherein c is 0.005 to 0.05 or 0.005 to 0.02.

108. The process according to embodiment 100, wherein the ratio $n_p:n_v$ of the molar amount $n_p$ of phosphorus present in the catalytically active material to the molar amount $n_v$ of V present in the catalytically active material is 0.09 to 2.0, preferably 0.9 to 1.5 and more preferably 0.9 to 1.2.

109. The process according to either of embodiments 100 or 108, wherein the elements other than vanadium and phosphorus present in the catalytically active material are one or more than one element from the group consisting of lithium, potassium, sodium, rubidium, cesium, thallium, molybdenum, zinc, hafnium, zirconium, titanium, chromium, manganese, nickel, copper, iron, boron, silicon, tin, niobium, cobalt and bismuth.

110. The process according to embodiment 109, wherein the total content of elements other than vanadium and phosphorus in the catalytically active material, based on the weight thereof, is not more than 5% by weight, calculating the particular element other than vanadium and phosphorus as the electrically neutral oxide in which the element has the same charge number as in the active material.

111. The process according to any of embodiments 100 to 110, wherein the arithmetic mean oxidation state of vanadium in the catalytically active material is +3.9 to +4.4 or +4.0 to +4.3.

112. The process according to any of embodiments 100 to 111, wherein the specific BET surface area of the catalytically active material is ≥15 to 50 m$^2$/g.

113. The process according to any of embodiments 100 to 112, wherein the total pore volume of the catalytically active material is 0.1 to 0.5 ml/g.

114. The process according to any of embodiments 100 to 113, wherein the total pore volume of the catalytically active material is 0.15 to 0.4 ml/g.

115. The process according to any of embodiments 100 to 114, wherein the at least one oxidation catalyst B is an unsupported catalyst or a supported catalyst.

116. The process according to embodiment 115, wherein the geometry of the unsupported catalyst is selected from the group consisting of sphere, ring and solid cylinder, and has a longest dimension in the range from 1 to 10 mm.

117. The process according to embodiment 115, wherein the geometry of the unsupported catalyst is a ring (a hollow cylinder) with an external diameter in the range from 3 to 10 mm, a height of 1 to 10 mm, an internal diameter of 1 to 8 mm and a wall thickness of 1 to 3 mm.

118. The process according to any of embodiments 100 to 114, wherein the at least one aldol condensation catalyst B is an eggshell catalyst which has the catalytically active material as an eggshell applied to the surface of an inert shaped support body.

119. The process according to embodiment 118, wherein the shaped support body is a sphere or a ring.

120. The process according to embodiment 118 or 119, wherein the longest dimension of the shaped support body is 1 to 10 mm.

121. The process according to any of embodiments 118 to 120, wherein the inert shaped support body is composed of steatite.

122. The process according to any of embodiments 118 to 121, wherein the thickness of the eggshell of active material is 10 to 2000 µm, or 10 to 500 µm, or 100 to 500 or 200 to 300 µm.

123. The process according to any of embodiments 1 to 122, wherein product gas mixture B is separated in separation zone T by passing product gas mixture B, optionally after direct and/or indirect cooling thereof, into a condensation column equipped with separating internals and fractionally condensing it within the condensation column and conducting streams X, Y and Z out of the condensation column as separate fractions.

124. The process according to any of embodiments 1 to 123, wherein product gas mixture B is separated in separation zone T by passing product gas mixture B, optionally after direct and/or indirect cooling thereof, into an absorption column equipped with separating internals in countercurrent to an organic solvent with a higher boiling point than acrylic acid at standard pressure, and absorbing the acetic acid and acrylic acid present in product gas mixture B into the solvent to obtain an absorbate, while a stream Z leaves the absorption column at the top thereof, and then removing streams X and Y from the absorbate as separate fractions by fractional distillation thereof in a rectification column.

125. The process according to any of embodiments 1 to 123, wherein product gas mixture B is separated in separation zone T by passing product gas mixture B, optionally after direct and/or indirect cooling thereof, into an absorption column equipped with separating internals in countercurrent to an aqueous solution as an absorbent, and absorbing the acetic acid and acrylic acid present in product gas mixture B into the solvent to obtain an absorbate, while a stream Z leaves the absorption column at the top thereof, and then removing streams X and Y as separate fractions from the absorbate by fractional distillation thereof in a rectification column.

126. Acrylic acid for which the ratio V of the molar amount $n^{14}C$ of $^{14}C$ atomic nuclei present in this acrylic acid to the molar amount $n^{12}C$ of $^{12}C$ atomic nuclei present in the same acrylic acid, $V=n^{14}C:n^{12}C$, is greater than 0 and less than the corresponding molar ratio V* of $^{14}C$ atomic nuclei to $^{12}C$ atomic nuclei present in the carbon dioxide in the earth's atmosphere.

127. Acrylic acid according to embodiment 126, wherein $V=(1/3)V^*$.

128. Acrylic acid according to embodiment 126, wherein $V=(2/3)V^*$.

129. A liquid phase P comprising at least 1 kg of acrylic acid, wherein the acrylic acid present is an acrylic acid according to any of embodiments 126 to 128.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing an acrylate product, the process comprising the steps of:
   (a) reacting, in a first reaction zone, a reaction gas mixture A comprising methanol, oxygen, and at least one diluent gas other than steam to form a product gas mixture A comprising formaldehyde, steam, and at least one inert diluent gas other than steam;
   (b) combining at least a portion of the product gas mixture A and acetic acid to form a reaction gas mixture B comprising acetic acid, formaldehyde, steam, and at least one diluent gas other than steam;
   (c) reacting, in a second reaction zone, at least a portion of the acetic acid in the reaction gas mixture B with at least a portion of the formaldehyde in the reaction gas mixture B to form a product gas mixture B comprising acrylic acid, acetic acid, steam, alkylenating agent, and at least one inert diluent gas other than steam; and
   (d) separating at least a portion of the product gas mixture B to form an alkylenating agent stream comprising at least 0.5 wt % alkylenating agent and less than 50 wt. % acetic acid and an intermediate acrylate product stream comprising acrylate product wherein the alkylenating agent is formaldehyde; and
   (e) separating the intermediate acrylate product stream to form a finished acrylate product stream comprising at least 85 wt % acrylic acid.

2. The process of claim 1, wherein the first reaction zone comprises at least one oxidation catalyst comprising a catalytically active material which is a mixed oxide of the general formula I $$[Fe_2(MoO_4)_3]_1[M^1{}_mO_n]_q \quad (I)$$

wherein:
$M^1$ is selected from the group consisting of:
Mo;
Fe; and
up to 10 mol % of one or more elements selected from the group consisting of Ti, Sb, Sn, Ni, Cr, Ce, Al, Ca, Mg, V, Nb, Ag, Mn, Cu, Co, Si, Na, K, Tl, Zr, W, Ir, Ta, As, P and B,
q is 0 to 5,
m is 1 to 3,
n is 1 to 6.

3. The process of claim 1, wherein the second reaction zone comprises at least one aldol condensation catalyst comprising a catalytically active material being a multi-element oxide active material of the general formula II $$V_1P_bFe_cX^1{}_dX^2{}_eO_n \quad (II)$$

wherein:
$X^1$ is Mo, Bi, Co, Ni, Si, Zn, Hf, Zr, Ti, Cr, Mn, Cu, B, Sn and/or Nb,
$X^2$ is Li, K, Na, Rb, Cs and/or Tl,
b ranges from 0.9 to 2.0
c ranges from 0 to 1,
d ranges from 0 to 0.1,
e ranges from 0 to 0.1, and
n is the stoichiometric coefficient of the element oxygen as determined by the stoichiometric coefficients of the non-oxygen elements and the charge numbers thereof.

4. The process of claim 1, wherein the product gas mixture B comprises at least 0.05 wt % alkylenating agent.

5. The process of claim 1, wherein step (d) is performed in at least one column.

6. The process of claim 1, wherein step (d) is performed in a two column system.

7. The process of claim 1, wherein step (d) yields at least one residue stream at a temperature ranging from 90° C. to 130° C. and/or a distillate stream at a temperature ranging from 60° C. to 90° C.

8. The process of claim 1, wherein step (d) is performed at a pressure ranging from 1 kPa to 300 kPa.

9. The process of claim 1, wherein step (e) comprises:
separating the intermediate acrylate product stream to form the finished acrylate product stream and a first finished acetic acid stream comprising acetic acid.

10. The process of claim 9, wherein at least a portion of the first finished acetic acid stream is recycled to the second reaction zone.

11. The process of claim 1, further comprising the step of:
separating the alkylenating agent stream to form a purified alkylenating stream comprising at least 1 wt % formaldehyde and a purified acetic acid stream comprising acetic acid and water.

12. The process of claim 11, wherein at least a portion of the purified alkylenating agent stream is recycled to the second reaction zone.

13. The process of claim 11, further comprising the step of:
separating the purified acetic acid stream to form a second finished acetic acid stream and a water stream.

14. The process of claim 13, wherein at least a portion of the second finished acetic acid stream is recycled to the second reaction zone.

15. The process of claim 1, further comprising the step of:
dehydrating the alkylenating agent stream to form a purified alkylenating stream comprising methanol and at least 1 wt % formaldehyde and a water stream.

16. The process of claim 15, wherein at least a portion of the purified alkylenating stream is recycled to the second reaction zone.

17. The process of claim 15, further comprising the step of:
separating the purified alkylenating agent stream to form a methanol stream and a purified alkylenating agent stream comprising formaldehyde.

18. The process of claim 17, wherein the purified alkylenating agent stream is recycled to the second reaction zone.

19. The process of claim 1, wherein the alkylenating agent stream comprises at least 1 wt % formaldehyde.

* * * * *